(12) United States Patent
Nitabach et al.

(10) Patent No.: US 7,192,773 B2
(45) Date of Patent: Mar. 20, 2007

(54) METHOD OF REDUCING NEURONAL ELECTRICAL ACTIVITY WITH A POTASSIUM CHANNEL SUBUNIT

(75) Inventors: Michael N. Nitabach, New York, NY (US); Justin Blau, New York, NY (US); Todd C. Holmes, New York, NY (US); Steven A. N. Goldstein, New York, NY (US)

(73) Assignee: New York University, New York, NY (US)

( * ) Notice: Subject to any disclaimer, the term of this patent is extended or adjusted under 35 U.S.C. 154(b) by 336 days.

(21) Appl. No.: 10/438,753

(22) Filed: May 15, 2003

(65) Prior Publication Data

US 2003/0237102 A1    Dec. 25, 2003

Related U.S. Application Data

(60) Provisional application No. 60/380,733, filed on May 15, 2002.

(51) Int. Cl.
*C12N 15/63* (2006.01)
*C12N 15/85* (2006.01)
*C12N 5/10* (2006.01)

(52) U.S. Cl. .................. 435/455; 435/320.1; 435/325; 435/348; 435/375

(58) Field of Classification Search ...................... None
See application file for complete search history.

(56) References Cited

OTHER PUBLICATIONS

Zilberberg et al., "Opening and claosing of KCNK0 potassium leak channels is tightly regulated," J. Gen. Physiol. 116: 721-734, Nov. 2000.*
Goldstein et al., "ORK1, a potassium-selective leak channel with two pore domains cloned from *Drosophila* melanogaster by expression in *Saccharomyces cerevisiae*," Proc. Natl. Acad. Sci. USA 93: 13256-13261, 1996.*
"Correction of Goldstein et al., Proc. Natl. Acad. Sci. USA 93: 13256-13261, 1996," Proc. Natl. Acad. Sci. USA 96: 318, 1999.*
Goldstein et al., GenBank Acc No. U55321, US Natl. Lib. of Med., Bethesda, MD, USA, Oct. 16, 2000, accessed by PTO Nov. 17, 2005.*
Orkin et al., Report and Recommendations of the Panel to Assess the NH Investment in Research on Gene Therapy, US National Institutes of Health, Bethesda, MD, Dec. 7, 1995.*
Verma et al., "Gene therapy—promises, problems and prospects," Nature 389: 239-242, 1997.*
Rosenberg et al., "Gene therapist, heal thyself," Science 287: 1751, 2000.*
Hsich et al., "Critical issues in gene therapy for neurologic disease," Hum. Gene Ther. 13:579-604, Mar. 2002.*
"Excitable cells", in Lecture Notes for Physics of the Human Body, Chap. 9, on http://galileo.phys.virgina.edu/classes/304/excite.pdf, accessed by the PTO on Apr. 28, 2006.*
Baines et al., Altered Electrical Properties in *Drosophila* Neurons Developing without Synaptic Transmission, J. Neuroscience, 21(5):1523-1531 (2001).
White et al., Targeted Attenuation of Electrical Activity in *Drosophila* Using a Genetically Modified $K^+$ Channel, Neuron, 31:699-711 (2001).
Nadeau et al., ROMK1 (Kir1.1) Causes Apoptosis and Chronic Silencing of Hippocampal Neurons, J. Neurophysiol., 84:1062-1075 (2000).
Kaneko et al., Disruption of Synaptic Transmission or Clock-Gene-Product Oscillations in Circadian Pacemaker Cells of *Drosophila* Cause Abnormal Behaviroal Rhythms, J. Neurobiol., 43:207-233 (2000).
Paradis et al., Homeostatic Control of Presynaptic Release Is Triggered by Postsynaptic Membrane Depolarization, Neuron, 30:737-749 (2001).
Johns et al., J. Inducible Genetic Suppression of Neuronal Excitability, Neuroscience, 19(5):1691-1697 (1999).

* cited by examiner

*Primary Examiner*—Scott D. Priebe
(74) *Attorney, Agent, or Firm*—Klauber & Jackson

(57) ABSTRACT

Methods of reducing the excitability of an excitable cell by transforming an excitable cell with a nucleic acid construct encoding an open rectifier $K^+$ channel (dORK) (SEQ ID NO:2) or a modified open rectifier $K^+$ channel (dORKΔ) (SEQ ID NO:4), and expressing the open rectifier $K^+$ channel in the excitable cell, wherein the excitability of the transformed cell is reduced. Also featured are transgenic animals expressing dORK or dORKΔ.

3 Claims, 12 Drawing Sheets

Conducting Pore dORKΔ-C Lines

Non-Conducting Pore dORKΔ-NC Lines

METHOD OF REDUCING NEURONAL ELECTRICAL ACTIVITY WITH A POTASSIUM CHANNEL SUBUNIT

This application claims priority under 35 USC § 119(e) from U.S Provisional Application Ser. No. 60/380,733 filed 15 May 2002, which application is herein specifically incorporated by reference in its entirety.

GOVERNMENTAL SUPPORT

This invention was made with partial assistance from grant No. IBN-0092753 from the National Science Foundation. The government may have certain rights in this invention.

BACKGROUND OF THE INVENTION

1. Field of the Invention

The present invention relates to a method of silencing neuronal electrical activity with a particular $K^+$ channel subunit. More specifically, the directed expression of a specific $K^+$ channel subunit may be used to modulate gene transcription and translation in neural cells, and transgenic animals expressing the specific open rectified $K^+$ channel subunit, dORK.

2. Statement of Related Art

Neurons and other excitable cells process information and control behavior via both short-term and long-term changes in the permeability of the cell membrane to various ions, and consequent changes in the electrical potential across the membrane. Various commercially and medically important pharmaceuticals act by modifying the electrical properties of excitable cells. For example, pharmacological blockers of voltage-gated calcium channels are widely used to reduce the excitability of the smooth muscle fibers that control dilation of arteries and arterioles, and thereby ameliorate hypertension and angina. Another approach to modifying cellular electrical excitability is the ectopic expression of ion channels themselves. For example, ectopic expression of potassium channels can both hyperpolarize the cell membrane and decrease its input resistance, thereby reducing cellular electrical excitability and preventing action potential generation.

Potassium channels cloned from insects have corresponding orthologs in mammalian species. See U.S. Pat. No. 5,559,026, which describes the isolation and characterization of DNA fragments encoding potassium channel genes from *Drosophila melanogaster* and *Caenorhabditis elegans*, and their expression in yeast, a model system in which to study potassium transport mechanics.

SUMMARY OF THE INVENTION

Improved methods or models for studying disorders of membrane excitability, such as epilepsies and cardiac arrhythmias would be useful for developing improved therapeutic methodologies. Several distinct exogenously-expressed potassium channels have been used to reduce cellular electrical excitability, both in transgenic animals and in cultured excitable cells. The present invention is based in part on the discovery that a particular potassium channel has specific biophysical properties that render it especially useful for the reduction of cellular electrical excitability. More specifically, the *Drosophila* open rectifier $K^+$ channel (dORK) (also known as "KCNK0") is unique in that it exhibits no voltage or time dependence of channel opening, and thus is able to act as a potassium-selective hole in the cell membrane.

Accordingly, in one aspect, the invention features a method of reducing or silencing the electrical activity of an excitable cell by providing a nucleic acid construct encoding an open rectifier $K^+$ channel (dORK) to an excitable cell, wherein dORK is expressed and the electrical activity of the excitable cell expressing dORK is reduced or silenced. In one embodiment, the nucleic acid construct encodes dORK comprising the sequence of SEQ ID NO:1. In one embodiment, the excitable cell is selected from a group consisting of a neuron, an endocrine secretory cell, a neuroendocrine secretory cell, a cardiac muscle fiber, a smooth muscle fiber, a skeletal muscle fiber, and a mast cell.

In a second aspect, the invention features a non-human transgenic animal expressing an exogenous nucleic acid sequence encoding an open rectifier potassium channel in a small subset of identified neurons. In a more specific embodiment, the exogenous nucleic acid sequence is the sequence of SEQ ID NO:1, encoding dORK (SEQ ID NO:2). In another embodiment, dORK is expressed in selected target neural cells. The transgenic animal of the invention is useful for studying the reduction of cellular electrical excitability because of the unique properties of dORK, a channel which does not exhibit voltage or time dependent channel opening, and thus acts as a potassium-selective hole in the cell membrane. In one embodiment, the non-human transgenic animal is selected from the group consisting of flies, mice, rats, rabbits, pigs, sheep, goats, and cows. In a specific embodiment, the non-human transgenic animal is a *Drosophila* fly. In another embodiment, dORK is expressed in pacemaker neuron cells. In a more specific embodiment, the pacemaker neuron cells are $LN_v$ cells.

The non-human transgenic animals of the invention can be used in drug assays and screens to identify a compound capable of modulating cellular electrical excitability mediated by dORK or a dORK-derived potassium channel. Accordingly, in a third aspect, the invention features an assay for identifying compounds capable of modulating cellular electrical excitability mediated by dORK or a dORK-derived potassium channel, comprising administering a test compound to a transgenic animal expressing an exogenous nucleic acid sequence encoding dORK or a dORK-derived potassium channel in an excitable cell, and determining if the test compound alters cellular excitability relative to cellular excitability measured in the absence of the test compound. Compounds identified as capable of modulating cellular electrical excitability mediated via dORK or a dORK-derived potassium channel are candidates for therapeutic application for diseases and conditions associated with cellular electrical excitability. A dORK-derived potassium channel includes the proteins having the amino acid sequences of SEQ ID NO:4 or SEQ ID NO:5.

In a fourth aspect, the invention features a method of reducing cellular excitability comprising providing a nucleic acid construct encoding a deletion mutant form of dORK lacking the entire C-terminal cytoplasmic regulatory domain ("dORK-delta" or "dORKΔ") under conditions wherein the nucleic acid construct is expressed in an excitable cell. The nucleic acid construct of the invention comprises the sequence of SEQ ID NO:3 and encodes the amino acid sequence of SEQ ID NO:4.

In a fifth aspect, the invention features a transgenic mammal expressing an exogenous nucleic acid sequence encoding a modified open rectifier potassium channel in a small subset of identified neurons. In a more specific embodiment, the exogenous nucleic acid sequence is the sequence of SEQ ID NO:3, encoding dORKΔ, a deletion mutant form of dORK which forms a constitutively open K+ channel (SEQ ID NO:4). The dORKΔ transgenic animal of the invention is particularly well-suited for the study of methods to reduce cellular excitability. In one embodiment, dORKΔ is expressed in selected target neural cells. In a more specific embodiment, dORK is expressed in pacemaker neuron cells. In an even more specific embodiment, the pacemaker neuron cells are $LN_v$ cells. In one embodiment of the transgenic animal of the invention, the animal is a *Drosophila* fly.

In another embodiment, the exogenous nucleic acid sequence encodes dORKΔ-NC which is a pore-mutant version of dORKΔ in which the Gly Tyr Gly and Gly Phe Gly motifs of the ion conduction pore have been mutated to AAA (SEQ ID NO:5). The dORKΔ-NC mutant is non-conducting and does not alter input resistance or resting potential. In a related aspect, the invention features a pore-mutant version of dORKΔ, termed dORKΔ-NC (SEQ ID NO:5).

The methods of the invention may be used to advantage as research tools for the analysis of the physiological role of particular neurons and neural circuits in the generation of particular animal behaviors. In addition, the invention is of immediate utility as a research tool in the analysis of the role of neuronal membrane electrical and ionic properties in bidirectional signal transduction pathways that link gene transcription, protein translation, and neuronal electrical signaling, as exemplified in Nitabach et al. (2002) Cell 109, 485–495, which publication is herein specifically incorporated by reference in its entirety.

Further, the methods of the invention are useful for the development of gene therapeutic techniques for the amelioration of human disorders relating to membrane excitability, including epilepsies and cardiac arrhythmias.

Other objects and advantages will become apparent from a review of the ensuing detailed description considered in conjunction with the following illustrative drawings.

DETAILED DESCRIPTION

Figure 1:
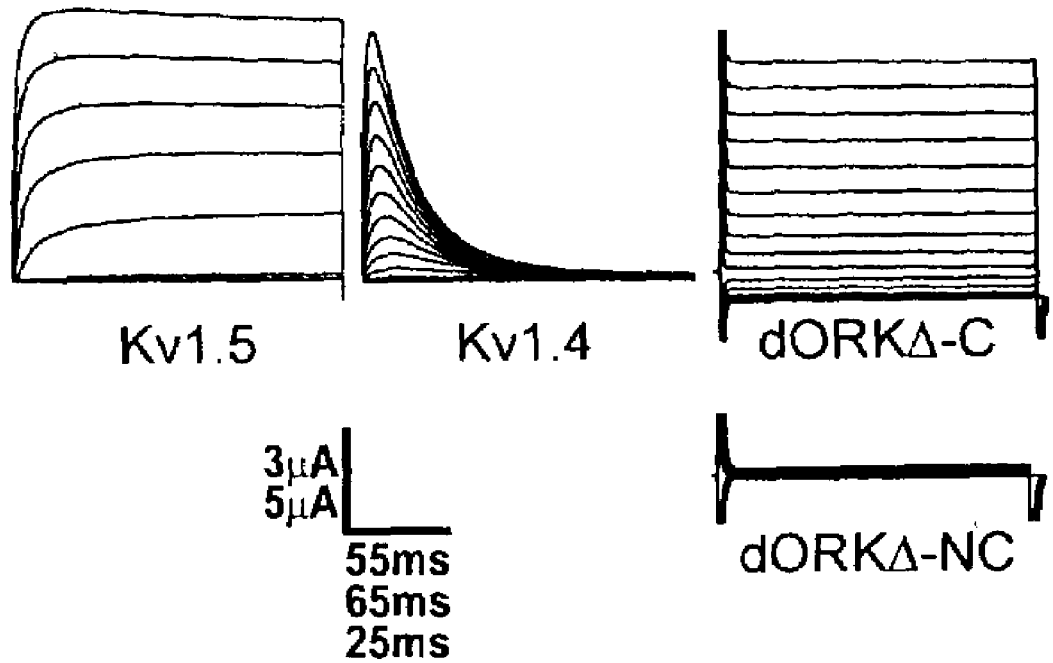
FIG. 1 shows a two-electrode voltage-clamp of macroscopic transmembrane currents of *Xenopus laevis* oocytes expressing K+ channel subunits evoked by a series of voltage steps.

Before the present methods are described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a method" includes one or more methods, and/or steps of the type described herein and/or which will become apparent to those persons skilled in the art upon reading this disclosure.

As used herein, a "functional fragment thereof" refers to a part or portion of a molecule which exhibits some or all of the activities of the full length molecule.

As used herein, the term "modified" is used to indicate that a molecule (e.g., a nucleic acid sequence or polypeptide) has been altered in such a manner to change a physical and/or functional property of the unaltered molecule. dORKΔ, for example, is a modified open rectifier potassium channel.

As used herein, the term "modulator" refers to a molecule (e.g., nucleic acid sequence, protein, peptide, agent, compound, or the like) capable of altering the activity of a molecule. Such modulators may act as antagonists or agonists of an activity of a such a molecule.

Unless defined otherwise, all technical and scientific terms used herein have the same meaning as commonly understood by one of ordinary skill in the art to which this invention pertains. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

General Description of the Invention

An important area of circadian rhythm research is the relationship between the function of the molecular clock in pacemaker neurons and the central physiological property that distinguishes neurons from other cells—regulated membrane electrical activity. Synaptic inputs are transduced through transient membrane currents, and downstream outputs are driven by firing action potentials. Activity-dependent free-running circadian rhythms in intracellular $Ca^{2+}$ levels and NMDA-evoked $Ca^{2+}$ currents have been observed in pacemaker neurons of the mammalian suprachiasmatic nucleus (SCN) (Coldwell (2000) Eur. J. Neurosci. 12:571–576; Coldwell (2001) Eur. J. Neurosci. 13:1420–1428). Clock-dependent circadian rhythms in ion channel mRNA abundance occur in *Drosophila* heads (Claridge-Chang et al. (2001) Neuron 32:657–671; McDonald and Rosbash (2001) Cell 107:567–578). Free-running circadian rhythms in membrane conductance and delayed-rectifier $K^+$ channel currents have been observed in pacemaker neurons of the molluscan retina (Michel et al. (1993) Science 259:239–241; Michel et al. (1999) J. Biol. Rhythms 14:141–150).

In the experiments described below, a reverse genetic approach was adopted in which either of two distinct $K^+$ channels was expressed in the pacemaker neurons of transgenic flies. It was found that an open rectified $K^+$ channel expressed in targeted neurons in transgenic animals results in electrical silencing of those neurons. Accordingly, generation of such transgenic animals is useful in the analysis of the physiological role of specific neurons and neural circuits involved in e.g., animal behavior and animal disorders.

Administration Methodology

In one embodiment, a nucleic acid comprising a sequence encoding dORK is administered. In another embodiment, a nucleic acid comprising a sequence encoding dORKΔ is administered. Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488–505; Wu and Wu (1991) Biotherapy 3:87–95; Tolstoshev (1993) Ann. Rev. Pharmacol. Toxicol. 32:573–596; Mulligan (1993) Science 260:926–932; and Morgan and Anderson (1993) Ann. Rev. Biochem. 62:191–217; and May (1993) TIBTECH 11(5): 155–215. Methods commonly known in the art of recombinant DNA technology of utility in the methods of the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In an aspect of the invention, the compound comprises a nucleic acid encoding the $K^+$ channel subunit dORK or the deletion mutant dORKΔ, such nucleic acid being part of an expression vector that expresses dORK or deletion mutant dORKΔ in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932–8935; Zijlstra et al. (1989) Nature 342: 435–438).

Expression of a nucleic acid sequence of the invention may be controlled by any promoter/enhancer element known in the art, but these regulatory elements must be functional in the host selected for expression. Promoters which may be used to control gene expression include, the SV40 early promoter region (Benoist and Chambon (1981) Nature 290: 304–310), the promoter contained in the 3' long terminal repeat of Rous sarcoma virus (Yamamoto et al (1980) Cell 22:787–797), the herpes thymidine kinase promoter (Wagner et al. (1981) Proc. Natl. Acad. Sci. U.S.A. 78.1441–1445), the regulatory sequences of the metallothionein gene (Brinster et al. (1982) Nature 296:39–42); prokaryotic expression vectors such as the beta-lactamase promoter (Villa-Kamaroff et al. (1978) Proc. Natl. Acad. Sci. U.S.A. 75:3727–3731), or the tac promoter (DeBoer et al. (1983) Proc. Natl. Acad. Sci. U.S.A. 80:21–25); see also "Useful proteins from recombinant bacteria" in Scientific American (1980) 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al. (1984) Cell 38:639–646; Ornitz et al. (1986) Cold Spring Harbor Symp. Quant. Biol. 50:399–409; MacDonald (1987) Hepatology 7:425–515); insulin gene control region which is active in pancreatic beta cells (Hanahan (1985) Nature 315:115–122), immunoglobulin gene control region which is active in lymphoid cells (Grosschedl et al. (1984) Cell 38:647–658; Adames et al. (1985) Nature 318:533–538; Alexander et al. (1987) Mol. Cell. Biol. 7:1436–1444), mouse mammary tumor virus control region which is active in testicular, breast, lymphoid and mast cells (Leder et al. (1986) Cell 45:485–495), albumin gene control region which is active in liver (Pinkert et al. (1987) Genes and Devel. 1:268–276), alpha-fetoprotein gene control region which is active in liver (Krumlauf et al. (1985) Mol. Cell. Biol. 5:1639–1648; Hammer et al. (1987) Science 235:53–58), alpha 1-antitrypsin gene control region which is active in the liver (Kelsey et al. (1987) Genes and Devel. 1:161–171), beta-globin gene control region which is active in myeloid cells (Mogram et al. (1985) Nature 315:338–340; Kollias et al. (1986) Cell 46:89–94), myelin basic protein gene control region which is active in oligodendrocyte cells in the brain (Readhead et al. (1987) Cell 48:703–712), myosin light chain-2 gene control region which is active in skeletal muscle (Sani (1985) Nature 314:283–286), and gonadotropic releasing hormone gene control region which is active in the hypothalamus (Mason et al. (1986) Science 234:1372–1378).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429–4432), which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.); and WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al. (1989) Nature 342: 435–438).

In a further embodiment, a viral vector, for example, a retroviral vector that contains a nucleic acid encoding dORK can be used (see Miller et al. (1993) Meth. Enzymol. 217:581–599). Such retroviral vectors have been modified to delete retroviral sequences that are not necessary for packaging of the viral genome and integration into host cell DNA. The nucleic acid encoding the polypeptide for use in gene therapy is cloned into the vector, which facilitates delivery of the gene into a subject. More information pertaining to retroviral vectors can be found, for example, in Boesen et al. (1994) Biotherapy 6:291–302, which describes the use of a retroviral vector to deliver the mdr1 gene to hematopoietic stem cells in order to render the stem cells more resistant to chemotherapy. Other references illustrating the use of retroviral vectors in gene therapy are: Clowes et al. (1994) J. Clin. Invest. 93:644–651; Kiem et al. (1994) Blood 83:1467–1473; Salmons and Gunzberg (1993) Human Gene Therapy 4:129–141; and Grossman and Wilson (1993) Curr. Opin. in Genetics and Devel. 3:110–114.

Adenoviruses are viral vectors that may also be used to advantage in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. In that adenoviruses are capable of infecting non-dividing cells, they may be of particular utility for those applications in which it is desirable to infect a non-proliferative cell type or population. Kozarsky and Wilson (1993) Current Opinion in Genetics and Development 3:499–503 present a review of adenovirus-based gene therapy. Bout et al. (1994) Human Gene Therapy 5:3–10 demonstrated the use of adenovirus vectors to transfer genes into the respiratory epithelia of rhesus monkeys. Other instances describing the use of adenoviruses in gene therapy are found in Rosenfeld et al. (1991) Science 252:431–434; Rosenfeld et al. (1992) Cell 68:143–155; Mastrangeli et al. (1993) J. Clin. Invest. 91:225–234; PCT Publication WO94/12649; and Wang et al. (1995) Gene Therapy 2:775–783. Moreover, adeno-associated viruses (AAV) have also been proposed for use in gene therapy (Walsh et al. (1993) Proc. Soc. Exp. Biol. Med. 204: 289–300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then selected to isolate those cells that have taken up and are expressing the transferred gene. Such selection methods are well known to those of skill in the art and described in a variety of publications, including, for example, Ausubel et al. (eds.), 1993, Current Protocols in Molecular Biology, John Wiley & Sons, NY; and Kriegler (1990) Gene Transfer and Expression, A Laboratory Manual, Stockton Press, NY. Selected cells are then delivered to a subject.

Methods for targeting a $K^+$ channel to excitable cells are known to the art, see for example, White et al. (2001) Neuron 31:699–711, and White et al. (2001) Current Biology 11:R1041–R1053, both of which publications are herein specifically incorporated by reference in their entirety.

The present invention also provides methods of preventing and/or treating disorders of a circadian rhythm which include depression, narcolepsy and jet lag. Such methods rely on temporary antagonisms to transiently inhibit the natural clock, and then supplying agonists to subsequently reset it e.g., for the treatment of jet lag. One such embodiment comprises administering to an animal a therapeutically effective amount of a nucleic acid encoding an open rectifier $K^+$ channel (dORK) or derivative or mutant thereof or an expression vector comprising a nucleic acid encoding an open rectifier $K^+$ channel (dORK) or derivative or mutant thereof. Also envisioned is administering to an animal a therapeutically effective amount of an open rectifier $K^+$ channel (dORK) or derivative or mutant thereof. Another such embodiment comprises administering to an animal a therapeutically effective amount of an agent capable of modulating the production and/or activity of an open rectifier $K^+$ channel. Yet another such embodiment comprises a mixture(s) of such agents.

Accordingly, it is a principal object of the present invention to provide an open rectifier $K^+$ channel (dORK) or derivative or mutant thereof in purified form that exhibit activities associated with circadian rhythms.

It is a further object of the present invention to provide a method and associated assay system for screening substances such as drugs, agents and the like, that are potentially effective in modulating the effects of open rectifier $K^+$ channels in mammals. Methods directed to identifying modulators (e.g., drugs, agents, and the like) of molecules involved in regulating circadian rythmn have been previously described, for example, in U.S. Pat. Nos. 6,476,188 and 6,057,129, the entire contents of which are incorporated herein by reference.

It is a still further object of the present invention to provide a method for the treatment of mammals to control depression, jet lag and/or narcolepsy.

It is a still further object of the present invention to provide pharmaceutical compositions for use in therapeutic methods which comprise or are based upon open rectifier $K^+$ channels or upon agents or drugs that control the production, or that mimic or antagonize the activities of the open rectifier $K^+$ channels.

Transgenic Animals

The invention features a non-human transgenic animal comprising a nucleic acid sequence (SEQ ID NO:1) encoding an open rectifier K+ channel, dORK (SEQ ID NO:2), a nucleic acid sequence (SEQ ID NO:3) encoding a modified open rectifier K⁺ channel, dORKΔ (SEQ ID NO:4), or a nucleic acid sequence in which a pore-mutant version of dORKΔ in which the GYG and GFG motifs of the ion conduction pores have been mutated to AAA (SEQ ID NO:5). In one embodiment, the transgenic animal is a fly, preferably a *Drosophila* fly. The transgenic animal of the present invention may also be a mouse, rat, rabbit, pig, goat, sheep, or monkey. In any case, the transgenic animals of the present invention can be used as research tools to investigate methods of reducing cellular electrical excitability in, for example, drug screens and assays which measure channel activity.

A transgenic animal can thus be prepared that expresses a dORK or dORKΔ. Such transgenic animals can be obtained through gene therapy techniques described herein or by microinjection of a nucleic acid, for example, into an embryonic stem cell or an animal zygote. Microinjection of BACs has been shown to be successful in a number of animals including rats, rabbits, pigs, goats, sheep, and cows (in Transgenic Animals Generation and Use ed., L. M. Houdebine (1997) Harwood Academic Publishers, The Netherlands). The BAC homologous recombination system described in Yu et al. (2000) Proc. Natl. Acad. Sci. USA 97:5978–5983 (herein specifically incorporated by reference in its entirety) was uniformly used through the studies described.

The GAL4 Expression System

Expressing a gene in cells in which it is not normally active is a powerful approach for determining its function. The GAL4 system allows the selective expression of any cloned gene in a wide variety of cell- and tissue-specific patterns in *Drosophila*. In brief, a promoter (or enhancer) directs expression of the yeast transcriptional activator GAL4 in a particular pattern, and GAL4 in turn directs transcription of the GAL4-responsive (UAS) target gene in an identical pattern. A key feature of the system relates to the independent expression of either the GAL4 gene or the UAS-target gene in distinct transgenic lines. In the GAL4 line, the activator protein is present, but the target gene, which is capable of being activated in the presence of the activator, is absent. In the UAS-target gene line, the target gene is present, but silent because the activator is not expressed. It is only when a GAL4 line is crossed to a UAS-target gene line that the target gene is activated and therefore expressed in the progeny. For a detailed description of the GAL4 system, which includes how to generate and characterize GAL4 lines and how to prepare UAS-target gene lines, see Phelps and Brand (1998) Methods: A Companion to Methods in Enzymology 14:367–379, herein specifically incorporated by reference in its entirety.

Specific Embodiments

Figure 2:
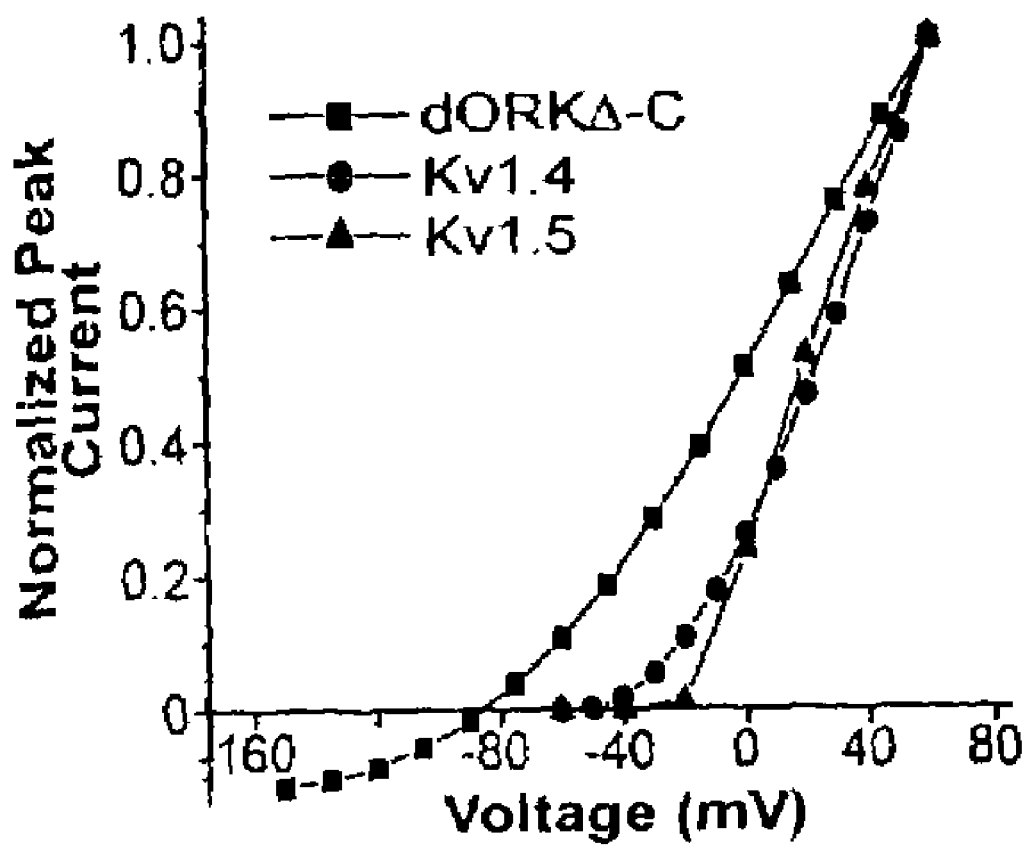
FIG. 2 shows normalized peak current-voltage (I–V) relationships for K+ channels expressed in oocytes. While Kv1.5 and Kv1.4 outward currents are absent below −20 mV or −40 mV, respectively, dORKΔ-C passes outward current down to −90 mV.
Figure 3:
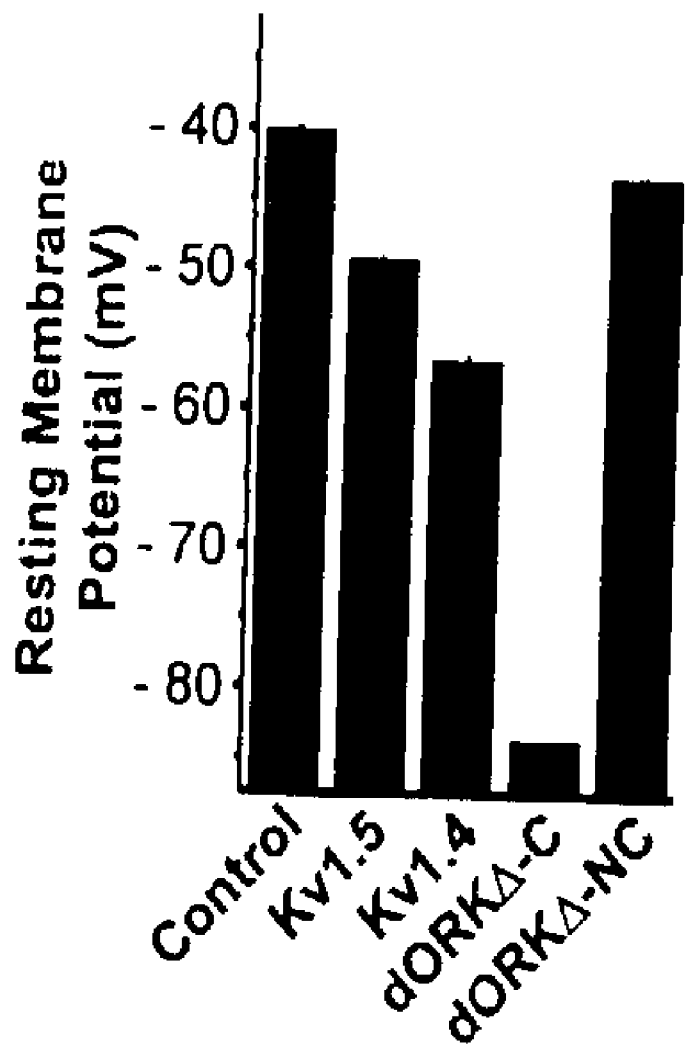
FIG. 3 shows the resting membrane potential of oocytes expressing K+ channels.

Neuronal Electrical Silencing With Modified *Drosophila* Open Rectifier K⁺ Channel (dORKΔ). The dORK K⁺ channel exhibits no voltage- or time-dependence of the open state and behaves as a K⁺-selective hole in the cell membrane, similar to the neuronal "leak" conductance (Goldstein et al. (1996) Proc. Natl. Acad. Sci. USA 93:13256–13261). The function of native dORK channels in *Drosophila* neurons is unknown, although modulation of biophysically similar channels controls resting potential and input resistance of mammalian neurons (Millar et al. (2000) Proc. Natl. Acad. Sci. USA 97:3614–3618; Talley et al. (2000) Neuron 25:399–410). While channels assembled from full-length dORK subunits are highly suppressed in the absence of serine phosphorylation of the C-terminal cytoplasmic domain, channels assembled from engineered truncated subunits (dORKΔ) are relieved of this suppression and thus constitutively open (Zilberberg et al. (2000) J. Gen. Physiol. 116:721–734).

dORKΔ expression in *Xenopus laevis* oocytes decreases input resistance between −40 and −60 mV, and drives the oocyte's normal resting potential of −40 mV down to −90 mV (FIGS. 2–3). This behavior is in contrast to that of voltage-gated K⁺ channels such as Kv1.4 and Kv1.5, which only weakly conduct at potentials below −40 mV (FIG. 2) and thus only weakly hyperpolarize the resting potential (FIG. 3). A pore-mutant version of dORKΔ in which the GYG and GFG motifs of the ion conduction pore were mutated to AAA (SEQ ID NO:5) was also generated as described herein. This mutant dORKΔ is non-conducting and does not alter input resistance or resting potential (dORKΔ-NC; FIGS. 1–3).

In contrast to voltage-gated K⁺ channels, dORKΔ channels are effective molecules for silencing neuronal activity. Of note, dORKΔ expression decreases the input resistance of a neuron at rest, at membrane potentials where most voltage-gated K⁺ channels have a low open probability. Decreased input resistance shunts synaptic currents and reduces their depolarizing effect. Moreover, dORKΔ expression pushes the resting potential of a neuron towards the K⁺ equilibrium potential, thereby increasing the depolarization required to trigger an action potential.

Figure 4:
FIG. 4 shows constructs used for P-element transformation of the *Drosophila melanogaster* germline. dORKΔ-C and dORKΔ-NC were expressed as enhanced GFP (eGFP) fusions from the UAS promoter, thus allowing cell-specific expression driven by GAL4.
Figure 4:

In order to demonstrate that dORKΔ is capable of acting as a neuronal silencer in vivo, the effects of pan-neuronal expression using the GAL4-UAS system (Brand and Perrimon (1993) Development 118:401–415, herein specifically incorporated by reference in its entirety) were evaluated. Flies were transformed with P elements comprising either the conducting dORKΔ (dORKΔ-C) or non-conducting dORKΔ-NC fused to enhanced GFP downstream of five GAL4 binding sites (UAS) (FIG. 4). Multiple independent chromosomal insertion lines containing UAS-dORKΔ-C or UAS-dORKΔ-NC were then crossed to flies containing an elav-GAL4 P element, which expresses GAL4 protein pan-neuronally (Lin and Goodman (1994) Neuron 13:507–523; Yao and White (1994) J. Neurochem. 63:41–51). Pan-neuronal expression of conducting dORKΔ-C resulted in 100% mortality. Indeed, dORKΔ-C-expressing flies from three independent insertion lines failed to reach adulthood, with the vast majority of embryos failing to hatch, and the rest exhibiting very sluggish movement as first instar larvae and then failing to reach second instar (data not shown). Pan-neuronal expression of the mammalian inward rectifier K⁺ channel, Kir2.1 (Baines et al. (2001) J. Neurosci. 21:1523–1531; Johns et al. (1999) J. Neurosci. 19:1691–1697), was also completely lethal (data not shown). Kir2.1, like dORK, has a substantial open probability at rest and has previously been demonstrated to silence *Drosophila* neurons electrically in vivo (Baines et al. (2001) supra). These effects of dORKΔ-C and Kir2.1 are consistent with the recent observation that elav-GAL4-driven expression of a modified voltage-gated K⁺ channel ("EKO") also increased mortality (White et al. (2001) Neuron 31:699–711). In contrast, pan-neuronal expression of non-conducting dORKΔ-NC did not result in an increase in mortality rate (data not shown).

The similarity in the effect of pan-neuronal dORKΔ-C expression with that of the expression of other K⁺ channels in *Drosophila* excitable cells (Baines et al. (2001) supra; Paradis et al. (2001) Neuron 30:737–749; White et al. (2001) supra) indicates that dORKΔ-C, like these other K$^+$ channels, is capable of silencing neuronal activity via an increase in membrane K$^+$ conductance at rest. This conclusion is further supported by the fact that no effects were seen following expression of non-conducting pore-mutant dORKΔ-NC, a transmembrane protein otherwise identical to dORKΔ-C.

Electrical Silencing of *Drosophila* Pacemaker Neurons is Not Cell-Lethal and Does Not Alter Cellular Morphology. In order to assess the role of neuronal electrical activity of pacemaker neurons in circadian locomotor rhythmicity and cycling of the molecular clock, dORKΔ-C, dORKΔ-NC, or Kir2.1 were expressed in pacemaker neurons using the clock cell-specific pdf-GAL4 driver (Renn et al. (1999) Cell 99:791–802. This driver line expresses GAL4 in the PDF-containing ventral subset of adult lateral pacemaker neurons (LN$_v$s, Helfrich-Forster (1995) Proc. Natl. Acad. Sci. USA 92:612–616) that are particularly important for controlling circadian locomotor rhythms (Blanchardon et al. (2001) Eur. J. Neurosci. 13:871–888; Renn et al. (1999) supra). Fluorescence microscopy of brain hemispheres confirms expression of GFP-tagged dORKΔ-C, dORKΔ-NC, and Kir2.1 solely in the LN$_v$s of UAS-dORKΔ-C;pdf-GAL4, UAS-dORKΔ-NC;pdf-GAL4, and UAS-Kir2.1;pdf-GAL4 flies, with GFP-tagged K$^+$ channel proteins visible in the LN$_v$ cell bodies and neuronal processes (data not shown). Of note, higher levels of expression were consistently observed for dORKΔ-C in the dORKΔ-C1 line in comparison to dORKΔ-C2, with dORKΔ-NC1 exhibiting similar expression to dORKΔ-C1 (data not shown).

Anti-PDF immunocytochemistry revealed that LN$_v$s expressing dORKΔ-C or Kir2.1 were present in normal numbers: about four small LN$_v$s and four large LN$_v$s per hemisphere, which exhibited their normal dorso-medial projection into the central brain (results not shown). While the processes of the dORKΔ-C- and Kir2.1-expressing LN$_v$s exhibited PDF-containing varicosities, they did not show the type of "beaded" morphology characteristic of necrotic and apoptotic neurons (Delisle and Carpenter (1984) J. Neurol. Sci. 63:241–250; Gold (1987) Toxicology 46:125–139; Svoboda et al. (2001) Development 128:3511–3520). Furthermore, the pattern of PDF staining can be observed in dORKΔ-C- and Kir2.1-expressing LN$_v$s of 30 day old flies (data not shown), indicating maintained survival of electrically silenced LN$_v$s. It is noteworthy that expression of dORKΔ-C or Kir2.1 neither killed the pacemaker neurons nor altered their normal projections, given the previous finding that ectopic Kir1.1 channel expression and concomitant increased K$^+$ efflux causes apoptosis of mammalian neurons (Nadeau et al. (2000) J. Neurophysiol. 84:106201075).

Figure 6:
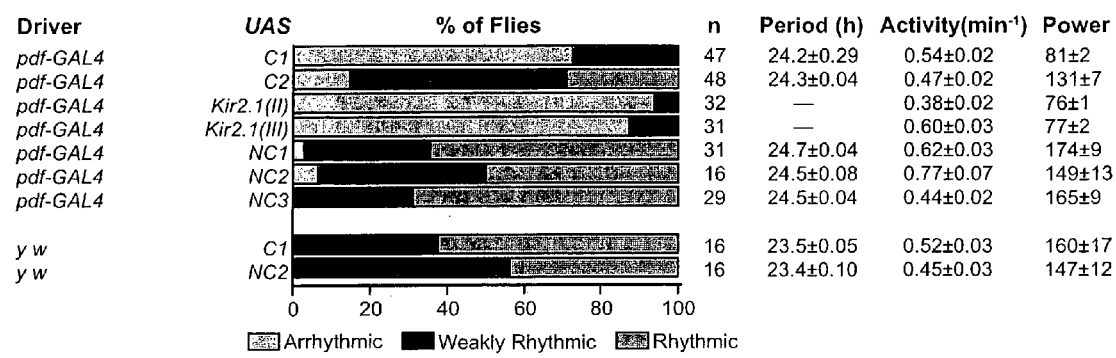
FIG. 6 presents a summary of behavioral data for flies of representative progeny of pdf-GAL4 or y w flies crossed to UAS-dORKΔ-C, UAS-Kir2.1, or UAS-dORKΔ-NC flies. Activity is in units of beam crosses per minute. Period, activity, and power are each mean±s.e.m.

Electrical Silencing of LN$_v$ Pacemaker Neurons Severely Impairs Free-Running Circadian Locomotor Rhythms. To test whether electrical silencing of pacemaker neurons impaired free-running circadian locomotor rhythms, the behavioral rhythms of flies expressing dORKΔ-C, dORKΔ-NC, or Kir2.1 in the LN$_v$s were examined using the pdf-GAL4 driver line. Most pdf-GAL4/dORKΔ-C1 flies were arrhythmic (72%), as were almost all pdf-GAL4/Kir2.1 flies from two independent Kir2.1 insertions (94% and 87%; FIG. 6). pdf-GAL4/dORKΔ-C2 flies exhibited a more modest deficit (15% arrhythmic; FIG. 6), consistent with reduced LN$_v$ dORKΔ-C expression in the C2 line as compared to that of C1. In contrast, only 3% of pdf-GAL4/NC flies tested were arrhythmic. The similar effects resulting from expression of Kir2.1 and dORKΔ-C in the LN$_v$ pacemaker cells, and the lack of effect of dORKΔ-NC expression, showed that behavioral arrhythmicity was due to increased resting K$^+$ conductance and consequent electrical silencing.

Figure 5:
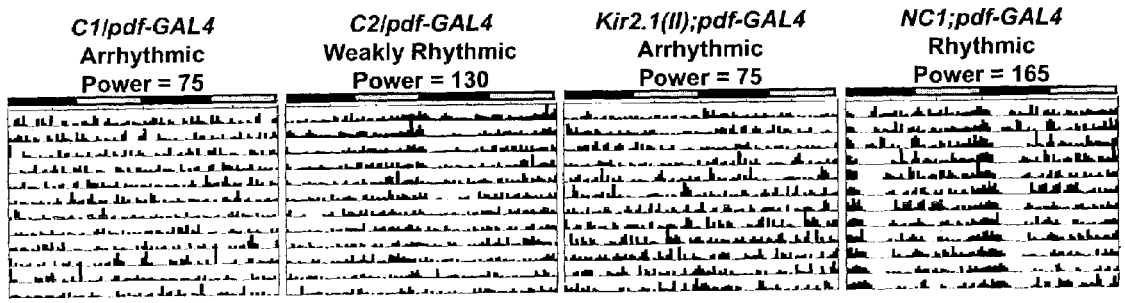
FIG. 5 shows locomotor actograms spanning 12 days in constant darkness (DD) of representative progeny of pdf-GAL4 or y w flies crossed to UAS-dORKΔ-C, UAS-Kir2.1, or UAS-dORKΔ-NC flies.

In order to quantify the differences in circadian rhythmicity between Kir2.1-, dORKΔ-C-, and dORKΔ-NC-expressing flies, a statistical analysis of each fly's circadian power was performed, a measure derived from chi-square periodogram analysis. C1, C2, and Kir2.1(II) and (III) lines exhibited significantly different average powers than each of the NC lines when driven by pdf-GAL4 (FIG. 6; ANOVA with Dunnett's T3 post-hoc paired comparison test, p<0.01). NC lines did not differ significantly from one another. These effects were due to GAL4-driven K$^+$ channel expression, and not due to a positional effect of P element insertion, since the rhythms of y w;C1 and y w;NC2 flies were statistically indistinguishable (FIG. 6). There were modest differences in average activity levels between some of the dORKΔ-C and dORKΔ-NC flies, but no visible gross deficits in locomotor behavior (FIGS. 5–6). These results demonstrated that electrical silencing of the LN$_v$s abolished circadian rhythms of locomotor behavior. Therefore, electrical activity in this small set of neurons plays an indispensable role in controlling circadian rhythmicity.

Electrical Silencing of LN$_v$ Pacemaker Neurons Stops the LN$_v$ Free-Running Molecular Clock. The abolition of circadian locomotor rhythms caused by pacemaker electrical silencing was consistent with an inability of the LN$_v$s to communicate with output pathways that ultimately drive locomotor activity. In order to determine whether electrical activity of the LN$_v$s also influenced cycling of the free-running intracellular clock, levels of TIM and PER proteins were assessed in LN$_v$s of adult flies expressing dORKΔ-C, dORKΔ-NC, or Kir2.1 driven by pdf-GAL4.

Figure 7:
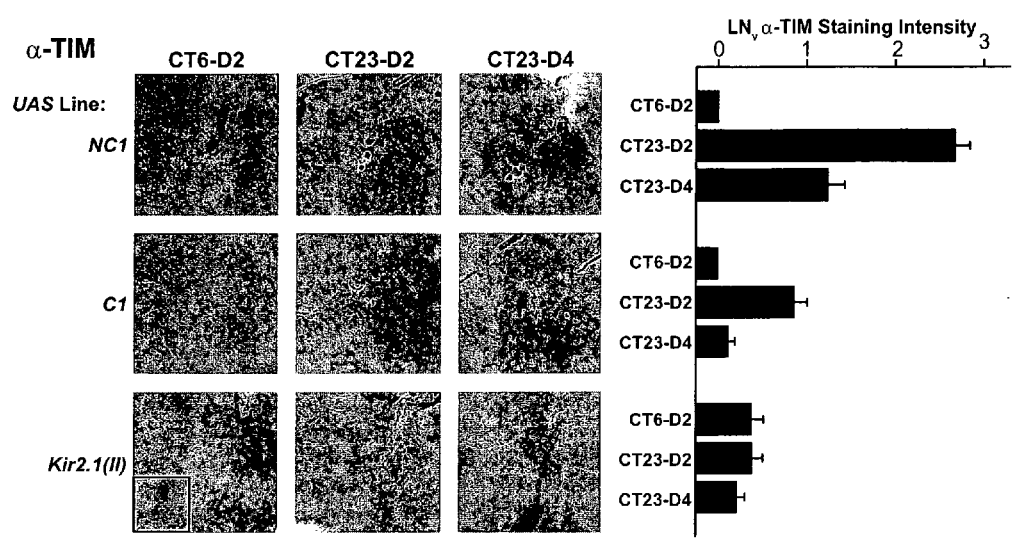
FIG. 7 depicts brains of the adult progeny of pdf-GAL4 flies crossed to UAS-dORKΔ-C, UAS-Kir2.1, or UAS-dORKΔ-NC flies, which were dissected and fixed at the circadian times indicated on either the second (D2) or fourth (D4) day of constant darkness, and processed for either anti-TIM or anti-PER immunocytochemistry and visualized using Nomarski optics.

Flies were entrained in light-dark (LD) cycles and then placed in constant darkness (DD) for either two or four days before immunocytochemistry. LN$_v$ TIM and PER levels were quantified using a scorer-blind subjective scale of staining intensity and analyzed by ANOVA. NC1 LN$_v$s showed strong circadian cycling of TIM and PER proteins with high levels in the nucleus at CT23 (just before subjective sunrise) and low levels at CT6 (subjective midday) or CT14 (shortly after subjective sunset) (FIG. 7). These data are consistent with observations of wild-type pacemaker neurons reported by Price et al. (1998) Cell 94:83–95 and Stanewsky et al. (1998) Cell 95:681–692.

Figure 8:
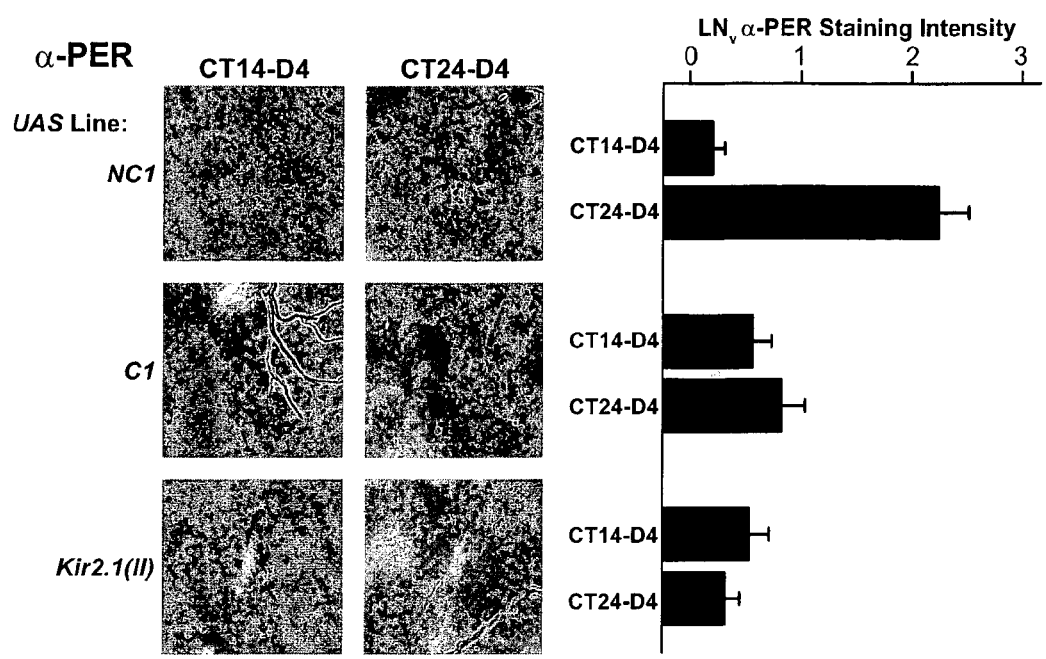
FIG. 8 illustrates anti-TIM immunocytochemistry of brains derived from adult progeny of pdf-GAL4 flies crossed to UAS-dORKΔ-C, UAS-Kir2.1, or UAS-dORKΔ-NC flies. $LN_v$s expressing dORKΔ-NC, dORKΔ-C or Kir2.1 are shown.

In contrast, the LN$_v$ clock in both C1 and Kir2.1(II) flies rapidly ran down in constant darkness. Nuclear TIM levels were significantly lower at CT23-D2 in C1 LN$_v$s than in NC1 LN$_v$s, and nearly undetectable in Kir2.1(II) LN$_v$s (FIG. 7). TIM declined to nearly undetectable levels in both C1 and Kir2.1(II) LN$_v$s by CT23-D4 (FIG. 7). PER cycling was affected similarly (FIG. 8). Interestingly, while TIM was never detectable in NC1 or C1 LN$_v$s at CT6, TIM was detectable at CT6 in the cytoplasm of some Kir2.1(II) LN$_v$s. The severity of the molecular phenotype exhibited by Kir2.1 (II) flies as compared to that of C1 flies was consistent with the relative severity of their behavioral phenotypes.

In order to more clearly assess the potential role of LN$_v$ electrical activity in the subcellular localization of clock proteins, anti-TIM immunocytochemistry was performed every six hours on day two in complete darkness. Brains were overstained to reveal the smaller quantities of TIM that normally accumulate in the cytoplasm early in subjective night. See FIG. 9. LN$_v$s expressing dORKΔ-NC exhibited a circadian rhythm of TIM subcellular localization, with TIM reaching peak cytoplasmic levels around CT16 (four hours after subjective lights-out), and then translocating almost completely to the nucleus by CT22. In contrast, $LN_v$s expressing Kir2.1 exhibited only a very weak circadian rhythm of TIM subcellular localization. TIM was detectable in the cytoplasm at all circadian time points, and only accumulated to very low levels in the nucleus at CT22. This suggested that $LN_v$ electrical activity may influence TIM nuclear entry.

Figure 9:
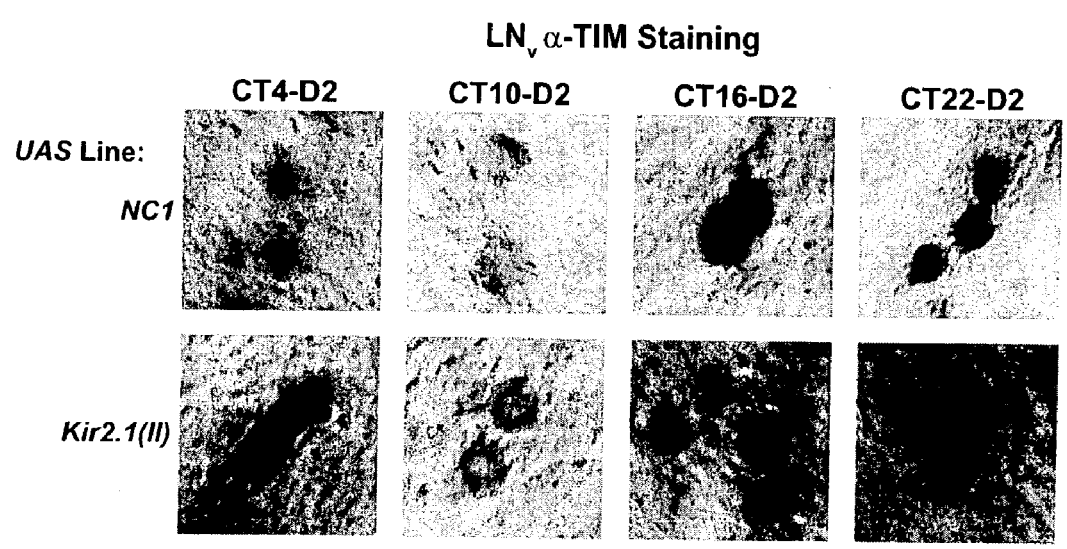
FIG. 9 shows anti-TIM immunocytochemistry of adult brains derived from adult progeny of pdf-GAL4 flies crossed to UAS-dORKΔ-C, UAS-Kir2.1, or UAS-dORKΔ-NC flies. The staining reveals the most commonly observed pattern of subcellular TIM localization.
Figure 11:
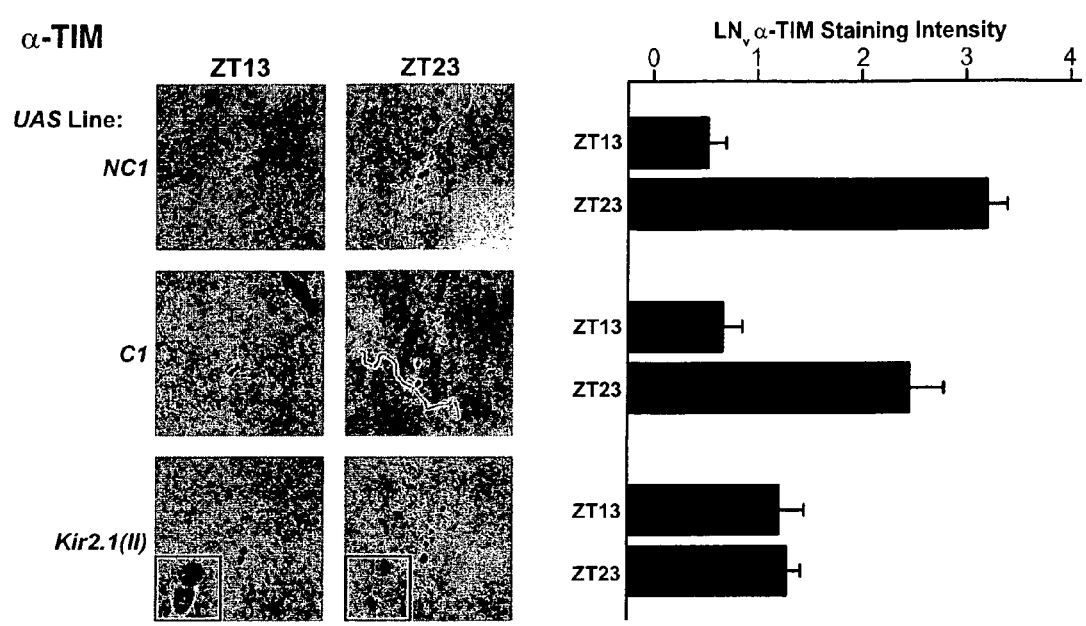
FIG. 11 depicts anti-TIM immunocytochemistry of adult brains.
Figure 12:
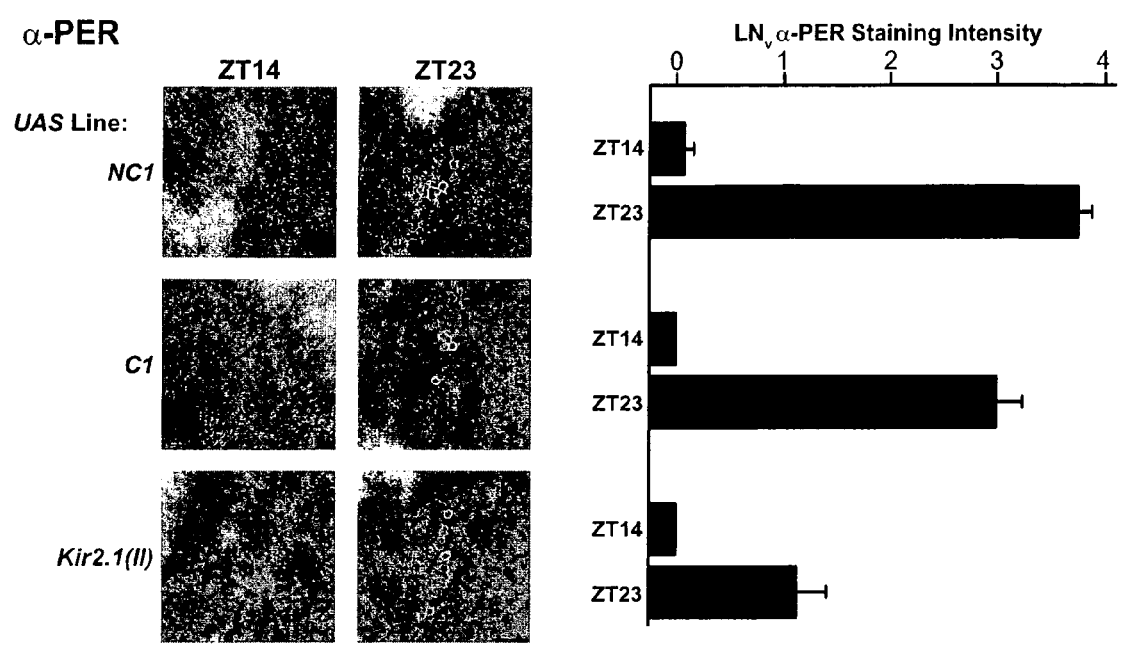
FIG. 12 shows anti-PER immunochemistry of adult brains.

Expression of dORKΔ or Kir2.1 in $LN_v$ Pacemaker Neurons Impairs Circadian Locomotor Rhythms in Light-Dark, But Does Not Stop the Light-Driven Molecular Clock. The results described above demonstrate that electrical activity in the PDF-expressing $LN_v$s is necessary for normal free-running of circadian behavioral rhythms and the $LN_v$ molecular clock. These results do not, however, address the role of pacemaker electrical activity in the light-driven clock. To this end, the effects of pacemaker electrical silencing on behavioral rhythms and molecular cycling in LD were examined. In contrast to the rundown and stopping of the molecular clock in DD, at least some core elements of the molecular clock of dORKΔ-C- or Kir2.1-expressing $LN_v$ pacemaker neurons continued to oscillate in LD. C1 $LN_v$s exhibited high TIM and PER levels in the nucleus at ZT23 (just before lights-on) that were statistically indistinguishable from those of NC1 $LN_v$s and low TIM and PER levels at ZT13 and ZT14, respectively (just after lights-off) (FIGS. 11–12). While $LN_v$ TIM levels were significantly lower at ZT23 in Kir2.1(II) flies than in NC1, and appeared to be higher than in NC1 at ZT13, the normal night-time transport of TIM protein from the cytoplasm to the nucleus still occurred. This was in contrast to the near absence of TIM nuclear transport in Kir2.1-expressing $LN_v$s during subjective night (FIG. 9).

Figure 10:
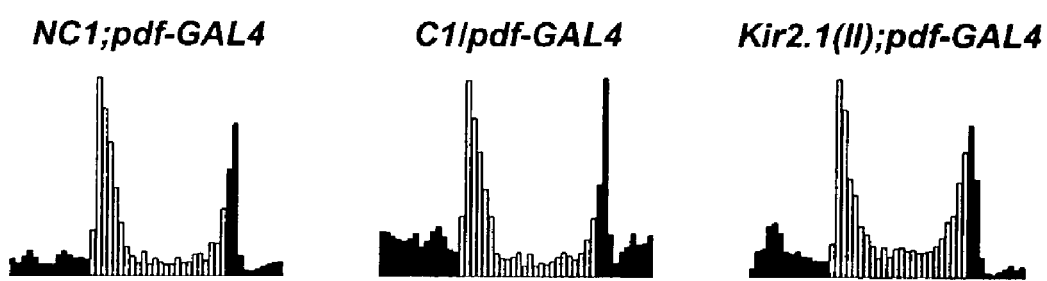
FIG. 10 shows activity vs. zeitgeber time plots averaged for 10 flies of each of the indicated genotypes assayed in light-dark (LD) cycles. Each bar represents 30 minutes of cumulative activity, with black bars indicating night, white indicating day.

Despite continued cycling of TIM and PER abundance and nuclear accumulation, the circadian behavior in LD of flies expressing Kir2.1 in the $LN_v$ pacemaker neurons was impaired. While NC1 and C1 flies, like wild-type flies (data not shown), began to increase their locomotor activity about two hours before lights-off, Kir2.1(II) flies began to increase their activity about four hours before lights-off (FIG. 10). This alteration in anticipatory behavior is similar to that observed in pdf$^{01}$ null mutant flies and flies lacking PDF-expressing $LN_v$s (Renn et al. (1999) Cell 99:791–802). A detectable deficit in Kir2.1(II) flies but not C1 flies was consistent with the more severe free-running behavioral and molecular phenotypes of Kir2.1(II), and could reflect more complete electrical silencing.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Methods and Materials

Amino acids 299–1001 were deleted from dORK (also known as KCNK0) (SEQ ID NO:2) by introduction of a stop codon in dORK cDNA to form dORKΔ (SEQ ID NO:4) (Zilberberg et al. (2000) J. Gen. Physiol. 116:721–734).

dORKΔ-NC (SEQ ID NO:5) was constructed by Quickchange (Stratagene) site-directed mutagenesis of both dORKΔ pore regions as follows: GYG107–109AAA and GFG219–221AAA. PCR-amplified eGFP (Clontech) coding sequence was ligated into a Not I site introduced using Quickchange between codons 288 and 289 of dORKΔ-C and dORKΔ-NC. GFP-tagged dORKΔ-C and dORKΔ-NC were subcloned into pCS2+ and pUAST plasmids for Xenopus oocyte expression and Drosophila P element transformation, respectively.

Oocyte Expression. Oocyte expression and two-electrode voltage clamp recording was performed in standard low-$K^+$ extracellular bath solution using standard procedures as described by Nitabach et al. (2001) Proc. Natl. Acad. Sci. USA 98:705–710. Drosophila embryos were microinjected with pUAST-dORKΔ-C or -NC constructs as described by Brand and Perrimon (1993) Development 118:401–415, to obtain multiple independent insertion lines of UAS-dORKΔ-C and -NC. elav-GAL4. The pdf-GAL4 and UAS-Kir2.1 lines are as described in Baines et al. (2001) Neurosci. 21:1523–1531; Lin and Goodman (1994) Neuron 22:645–648; Renn et al. (1999) Cell 99:791–802).

Circadian Behavioral Analysis. Locomotor activity of individual flies was measured using the TriKinetics infrared beam-crossing system recording total crosses in 30 minute bins. Raw activity histograms were analyzed for circadian rhythms using Actimetrics Clocklab software. Chi-square periodograms were constructed according to Sokalove and Bushell (1978) J. Theoretical Biol. 72:131–160, and significant circadian rhythmicity was defined as the presence of a peak in periodogram power that extends above the $\alpha=0.01$ chi-square significance line. Since this line is equal to a power of 75 at a period of 24 hours, flies with no periodogram peak crossing the significance line were assigned a circadian power of 75. This would tend to overestimate the circadian power of these flies, and thus is conservative with regard to assessing statistical differences in power between genotypes exhibiting frequent arrhythmicity and those that are predominately rhythmic.

Methodological details pertaining to FIG. 6, for example, are as follows: activity is shown in units of beam crosses per minute and period, activity, and power are each mean±s.e.m. Statistical analysis of circadian locomotor rhythms were determined using ANOVA with Dunnett's T3 post-hoc paired comparison test, p<0.01.

In FIG. 10, activity vs. zeitgeber time plots were averaged for 10 flies of each of the indicated genotypes assayed in LD. Each bar represents 30 minutes of cumulative activity, with black bars indicating night, white indicating day.

Immunocytochemistry. Adult brains were processed for anti-TIM, anti-PER, and anti-PDF immunocytochemistry using the same antibodies as described Price et al. (1998) Cell 94:83–95. Staining intensity of the most darkly stained $LN_v$ in each brain hemisphere was quantified on a scale from 0 to 4 by a scorer blind to the experimental group to which any particular brain belonged and wherein 0 denotes undetectable staining, 1 denotes just barely detectable, and 4 denotes maximal staining. This is the standard method for quantifying clock protein expression in Drosophila pacemaker neurons (Kaneko et al. (1997) J. Neurosci. 17:6745–6760; Stanewsky et al. (1998) Cell 95:681–692. Images shown were selected as representative of the mean staining intensity for each experimental condition. In some panels, nerves can be seen on the surface of the brain which were not stained, but appeared dark in the Nomarski optics.

Introduction

Animals exhibit roughly 24 hour (circadian) cycles of rest and activity even when "free-running" in complete darkness. Oscillating gene expression is a universal feature of the molecular clocks that regulate circadian behavioral rhythms, with the best understood molecular clock that of *Drosophila* (reviewed in Reppert and Weaver (2000) J Biol Rhythms 15, 357–64; Williams and Sehgal (2001) Annu Rev Physiol 63, 729–55; Young and Kay (2001) Nat Rev Genet 2, 702–15). Molecular and genetic analyses of period, timeless, and other clock genes have demonstrated that self-sustaining cell-autonomous interlocking feedback loops of transcription and translation generate intracellular circadian rhythms in the abundance, phosphorylation state, and nuclear localization of PERIOD (PER) and TIMELESS (TIM) proteins (Young and Kay (2001) supra). This feedback loop, and hence behavioral rhythms, can be reset by light-induced TIM degradation (reviewed in Young (1998) Annu Rev Biochem 67, 135–52).

Rhythmic cycles of clock gene expression and subcellular localization are found in a set of pacemaker neurons that control circadian rhythms of locomotor activity in *Drosophila* (Blanchardon et al. (2001) Eur J Neurosci 13, 871–88; Kaneko et al. (2000b) J Neurobiol 43, 207–33; Renn et al. (1999) Cell 99, 791–802). These pacemaker cells receive light inputs via neuronal signals originating in the eyes, and by cell-autonomous expression of CRYPTOCHROME (CRY), a blue-light photoreceptor protein (Emery et al. (1998) Cell 95, 669–79; Emery et al. (2000) Neuron 26, 493–504; Stanewsky et al. (1998) Cell 95, 681–92). Either of these signals is sufficient to entrain behavioral rhythms (Helfrich-Forster et al. (2001) Neuron 30, 249–61). Some pacemaker cells produce a neuropeptide, PIGMENT DISPERSING FACTOR (PDF), which is likely to function as a circadian output signal (Park et al. (2000) Proc Natl Acad Sci USA 97, 3608–13; Renn et al. (1999) supra).

An important area of circadian rhythm research is directed to understanding the relationship between the function of the molecular clock in pacemaker neurons and the regulated membrane electrical activity of these neurons. In brief, synaptic inputs are transduced through transient membrane currents, and downstream outputs are driven by firing action potentials. Despite considerable experimental effort and numerable publications directed to this subject, the role of synaptic inputs to pacemaker neurons in the establishment and maintenance of the intracellular molecular clock, the role of the molecular clock in controlling the electrical activity of pacemakers, and the effect mediated by electrical activity of pacemaker neurons on in vivo oscillations of the molecular clock remain undefined.

As described herein, a reverse genetic approach was utilized to address the interrelatedness of $K^+$ channel-mediated electrical silencing of pacemaker neurons and circadian locomotor rhythms. The results presented herein indicate that pacemaker cell electrical activity acts as part of a feedback loop that is necessary for the cycling of the free-running clock.

Results

FIG. 1 shows a two-electrode voltage-clamp of macroscopic transmembrane currents of *Xenopus laevis* oocytes expressing $K^+$ channel subunits evoked by a series of voltage steps. The vertical scale bar is 3 μA for Kv1.5 and Kv1.4, and 5 μA for dORKΔ-C and -NC. The horizontal scale bar is 55 ms, 65 ms, and 25 ms, for Kv1.5, Kv1.4, and dORKΔ (both -C and -NC), respectively. The results demonstrate that dORKΔ expression in *Xenopus laevis* oocytes decreased input resistance between −40 and −60 mV, and drove the oocyte's normal resting potential of −40 mV down to −90 mV, the Nernst equilibrium potential for $K^+$. See FIGS. 1–3. In contrast, the voltage-gated $K^+$ channels, such as Kv1.4 and Kv1.5, only weakly conduct at potentials below −40 mV (FIG. 2) and thus only weakly hyperpolarize the resting potential (FIG. 3). A pore-mutant version of dORKΔ, in which the GYG and GFG motifs of the ion conduction pore were mutated to AAA, was non-conducting and did not alter input resistance or resting potential (dORKΔ-NC; FIGS. 1–3). Bars shown in FIG. 3 depict average±s.e.m. currents (n>20 oocytes for each channel).

To evaluate the ability of dORKΔ to act as a neuronal silencer in vivo, the effects of pan-neuronal expression using the GAL4-UAS system (Brand and Perrimon (1993) Development 118:401–415) were examined. Flies were transformed with P elements with either the conducting dORKΔ (dORKΔ-C) or non-conducting dORKΔ-NC fused to enhanced GFP downstream of five GAL4 UAS binding sites. See FIG. 4. Multiple independent chromosomal insertion lines containing UAS-dORKΔ-C or UAS-dORKΔ-NC were then crossed to flies containing an elav-GAL4 P element, which expresses GAL4 protein pan-neuronally (Lin and Goodman (1994) Neuron 13:507–523; Yao and White (1994) J. Neurochem. 63:41–51). In summary, pan-neuronal expression of conducting dORKΔ-C resulted in 100% mortality. dORKΔ-C-expressing flies from three independent insertion lines failed to reach adulthood. The vast majority of embryos failed to hatch, and the rest exhibited very sluggish movement as first instar larvae and then failed to reach second instar (data not shown).

To test whether electrical silencing of pacemaker neurons impaired free-running circadian locomotor rhythms, an assessment was made of the behavioral rhythms of flies expressing dORKΔ-C, dORKΔ-NC, or Kir2.1 in the $LN_v S$ using the pdf-GAL4 driver line. FIG. 5 shows locomotor actograms spanning 12 days in constant darkness (DD) of representative progeny of pdf-GAL4 or y w flies crossed to UAS-dORKΔ-C, UAS-Kir2.1, or UAS-dORKΔ-NC flies. In FIG. 5, power is depicted as the height in arbitrary units of the periodogram peak calculated by chi-square analysis, and is a quantification of the strength of the circadian rhythm over the 15 day measurement period. The power of each arrhythmic fly was defined as 75, which is the p<0.01 significance threshold for a period of 24 h. Flies exhibiting a power greater than 150 were defined as rhythmic, while those with power between 75 and 150 were defined as weakly rhythmic. The bar above each actogram indicates subjective day (gray) and subjective night (black).

As shown in FIG. 5, most pdf-GAL4/dORKΔ-C1 flies were arrhythmic (72%), as were almost all pdf-GAL4/Kir2.1 flies derived from two independent Kir2.1 insertions (94% and 87%). pdf-GAL4/dORKΔ-C2 flies exhibited a more modest deficit (15% arrhythmic), consistent with reduced $LN_v$ dORKΔ-C expression in the C2 line as compared to C1, whereas only 3% of pdf-GAL4/NC flies tested were arrhythmic. See FIG. 5. These results demonstrate that behavioral arrhythmicity is due to increased resting $K^+$ conductance and consequent electrical silencing.

In order to quantify the differences in circadian rhythmicity between Kir2.1-, dORKΔ-C-, and dORKΔ-NC-expressing flies, a statistical analysis of each fly's circadian power was performed using a measure derived from chi-square periodogram analysis (see Methods and Materials above). C1, C2, and Kir2.1(II) and (III) lines exhibited significantly different average powers than each of the NC lines when driven by pdf-GAL4 (FIG. 6; ANOVA with Dunnett's T3 post-hoc paired comparison test, p<0.01). NC lines did not differ significantly from one another. See FIG. 6. These effects were a consequence of GAL4-driven $K^+$ channel expression, and not due to a positional effect of P element insertion, since the rhythms of y w;C1 and y w;NC2 flies were statistically indistinguishable. See FIG. 6. There were modest differences in average activity levels among some of the dORKΔ-C and dORKΔ-NC flies, but no visible gross deficits in locomotor behavior. See FIGS. 5 and 6. These results indicated that electrical silencing of the $LN_v$s abolishes circadian rhythms of locomotor behavior. Therefore, electrical activity in this small set of neurons plays an indispensable role in controlling circadian rhythmicity.

In order to determine whether electrical activity of the $LN_v$s also influences cycling of the free-running intracellular clock, levels of TIM and PER proteins were assessed in $LN_v$s of adult flies expressing dORKΔ-C, dORKΔ-NC, or Kir2.1 driven by pdf-GAL4. In brief, flies were entrained in LD cycles and then placed in DD for either two or four days before immunocytochemistry. Brains of the adult progeny of the above indicated crosses were dissected and fixed at the circadian times indicated on either the second (D2) or fourth (D4) day of constant darkness, and processed for either anti-TIM or anti-PER immunocytochemistry. Anti-TIM or -PER staining intensity of the darkest staining $LN_v$ of each brain hemisphere was assessed by blind scoring using a subjective intensity scale from 0 to 4, with 0 being undetectable, 1 being just-detectable and 4 being maximal. At least 12 hemispheres were analyzed for each genotype and time-point. Bar graphs depict mean±s.e.m. staining intensity scores. The $LN_v$ TIM and PER levels quantified using the above indicated scorer-blind subjective scale of staining intensity were analyzed by ANOVA with Dunnett's T3 post-hoc paired comparison test. Bar graphs depict mean±s.e.m. staining intensity scores. NC1 $LN_v$s showed strong circadian cycling of TIM and PER proteins with high levels in the nucleus at CT23 (just before subjective sunrise) and low levels at CT6 (subjective midday) or CT14 (shortly after subjective sunset). See FIG. 7.

In contrast, the $LN_v$ clock in both C1 and Kir2.1(II) flies rapidly ran down in constant darkness. Nuclear TIM levels were significantly lower at CT23-D2 in C1 $LN_v$s than in NC1 $LN_v$s, and nearly undetectable in Kir2.1(II) $LN_v$s. Moreover, TIM declined to nearly undetectable levels in both C1 and Kir2.1(II) $LN_v$s by CT23-D4. See FIG. 7. PER cycling was similarly affected. See FIG. 8. Although TIM was never detectable in NC1 or C1 $LN_v$s at CT6, TIM was detectable at CT6 in the cytoplasm of some Kir2.1(II) $LN_v$s. See FIG. 7, inset. In summary, the severity of the molecular phenotype of a strain was, in general, correlated with the behavioral phenotype of the strain. See FIGS. 5 and 6.

To address the role of pacemaker electrical activity in the light-driven clock, the effects of pacemaker electrical silencing on behavioral rhythms and molecular cycling in LD were assessed. In contrast to the behavior of the molecular clock in DD, at least some core elements of the molecular clock of dORKΔ-C- or Kir2.1-expressing $LN_v$ pacemaker neurons continued to oscillate in LD. As demonstrated herein, C1 $LN_v$s exhibited high TIM and PER levels in the nucleus at ZT23 (just before lights-on) that were statistically indistinguishable from those of NC1 $LN_v$s and low TIM and PER levels at ZT13 and ZT14, respectively (just after lights-off). See FIGS. 11 and 12 wherein the results depicted were derived from at least 12 hemispheres for each genotype and time-point. Thus, while $LN_v$ TIM levels were significantly lower at ZT23 in Kir2.1(II) flies than in NC1, and appeared to be higher than in NC1 at ZT13, the normal night-time transport of TIM protein from the cytoplasm to the nucleus was maintained. See FIG. 11, insets.

Despite continued cycling of TIM and PER abundance and nuclear accumulation, the circadian behavior in LD of flies expressing Kir2.1 in the $LN_v$ pacemaker neurons was impaired. While NC1 and C1 flies, like wild-type flies (data not shown), began to increase their locomotor activity about two hours before lights-off, Kir2.1(II) flies began to increase their activity about four hours before lights-off. See FIG. 10. This alteration in anticipatory behavior likely reflects a greater degree of electrical silencing in Kir2.1(II) flies.

Discussion

As shown herein, electrical activity was identified as a novel functional component of the molecular clock of the $LN_v$ pacemaker neurons. The prevailing view in the scientific literature prior to the discovery of the present invention, however, was that electrical-activity of the $LN_v$s, while involved in entrainment and circadian behavior, was not likely to play a role in intracellular molecular oscillations. It was thus surprising to observe that electrical silencing of the $LN_v$s stops their free-running molecular clock. On the basis of this finding, the present inventors propose that electrical activity is a necessary component of the cell-autonomous feedback loops in the $LN_v$ molecular clock, along with the essential transcription factors and regulatory enzymes that have been previously identified.

In order to address the role of electrical activity of the pacemaker neurons in circadian rhythms, the present inventors employed a method for neuronal electrical silencing based upon UAS/GAL4-mediated targeted expression of either of two distinct $K^+$ channels. Such manipulations of membrane properties have been shown to be highly effective at shunting synaptic inputs and silencing activity, both in mammalian and *Drosophila* excitable cells (Baines et al. (2001) J Neurosci 21, 1523–31; Johns et al. (1999) J Neurosci 19, 1691–7; Nadeau et al. (2000) J Neurophysiol 84, 1062–75; Paradis et al. (2001) Neuron 30, 737–49; White et al. (2001) Neuron 31, 699–711).

Two approaches were used to demonstrate that effects of $K^+$ channel expression in the pacemaker neurons result from electrical silencing. First, the developmental and behavioral effects of pan-neuronal expression of dORKΔ-C, the Kir2.1 inward rectifier, and the "EKO" modified voltage-gated $K^+$ channel were compared. Kir2.1 and EKO have each been demonstrated to silence electrical activity in *Drosophila* neurons and other excitable cells (Baines et al., 2001, supra; Paradis et al., 2001, supra; White et al., 2001, supra). Pan-neuronal expression of either dORKΔ-C or Kir2.1 leads to nearly complete lethality, with few larvae hatching from their egg cases and those that do exhibiting extreme sluggishness (data not shown). Second, an otherwise-identical non-conducting pore mutant version of dORKΔ (dORKΔ-NC) was generated to provide a negative experimental control. Since dORKΔ-NC-expressing neurons behaved in all respects as wild-type (FIGS. 1–12), it was apparent that the effects of dORKΔ-C or Kir2.1 were due to an increase in $K^+$ conductance at rest—an alteration in membrane properties known to silence electrical activity both in mammalian and *Drosophila* neurons (Baines et al., 2001, supra; Johns et al., 1999, supra; Nadeau et al., supra, 2000; Paradis et al., 2001, supra; White et al., 2001, supra).

One potential difficulty with the use of $K^+$ channels for silencing neuronal electrical activity is the possibility that excessive $K^+$ efflux may lead to cell death (Nadeau et al., 2000, supra). The present inventors have demonstrated that $LN^v$ pacemaker neurons expressing dORKΔ-C or Kir2.1 are present in their ordinary number, appear healthy, and exhibit their normal dorso-medial projection into the central brain. Projections of dORKΔ-C- or Kir2.1-expressing pacemakers were not observed to exhibit the type of "beading" that is a morphological hallmark of neuronal necrosis and apoptosis (Delisle and Carpenter (1984) J Neurol Sci 63, 241–50; Gold, (1987) Toxicology 46, 125–39; Svoboda et al. (2001) Development 128, 3511–20). dORKΔ-C- and Kir2.1-expressing $LN_v$ pacemakers continue to synthesize PDF and to transport it down their axonal processes, and dORKΔ-C- and Kir2.1-expressing $LN_v$s still exhibit oscillation and nuclear entry of TIM and PER in LD (FIGS. 10–12). Thus, pacemaker neurons expressing dORKΔ-C or Kir2.1 are viable and possess a molecular clock capable of oscillating. This is an important finding with regard to the therapeutic applications described herein.

Results presented herein establish that electrical activity in the PDF-expressing subset of pacemaker neurons is required for generation of circadian locomotor rhythms (FIGS. 4–5). Also examined was the role of pacemaker electrical activity in free-running circadian molecular oscillations. When dORKΔ-C or Kir2.1 is expressed in the $LN_v$ pacemaker neurons, the $LN_v$ molecular clock runs down and ultimately stops in DD (FIGS. 7–8). The rapidity of the rundown correlates with the relative severity of behavioral phenotypes seen in lines C1 and Kir2.1(II) (FIGS. 5, 6, 10–12). Furthermore, electrical silencing interferes with normal nuclear translocation of TIM in free-running conditions, but not in LD (FIGS. 9–12). In contrast, dORKΔ-NC expression has no effect on the normal cycling of $LN_v$ TIM and PER levels in DD (FIGS. 7–8), nor on the nuclear translocation of TIM (FIG. 9). These results indicate a hitherto unexpected role for pacemaker electrical activity in the cycling of the free-running intracellular molecular clock.

Blocking pacemaker synaptic output with tetanus toxin, while inducing behavioral arrythmicity, has no effect on molecular oscillation (Kaneko et al. (2000) J Neurobiol 43, 207–33). This suggests that stopping the clock through pacemaker electrical silencing is not mediated by consequent silencing of synaptic outputs. Furthermore, in the complete absence of entraining light-driven inputs, the pacemaker molecular clock continues to oscillate (Helfrich-Forster et al. (2001) Neuron 30, 249–61). In combination with these studies, the results presented herein suggest that neuronal electrical activity plays independent roles in pacemaker output signaling and oscillation of the intracellular clock, and point to a potentially cell-autonomous function in the free-running $LN_v$ molecular clock.

Pacemaker electrical silencing also causes deficits in circadian behavior in LD; while wild-type and dORKΔ-NC-expressing flies show an increase in locomotor activity beginning about two hours before lights-off, flies expressing Kir2.1 in the $LN_v$s increase their activity about four hours before lights-off (FIGS. 10–12), thereby phenocopying $pdf^{01}$ null mutant flies and flies lacking PDF-expressing $LN_v$s (Renn et al. (1999) Cell 99, 791–802). This behavioral alteration indicates that electrical silencing still occurs in LD. Some core elements of the molecular clock, however, still oscillate in abundance and subcellular localization in LD, with high levels of both TIM and PER in the nuclei of Kir2.1-expressing larval $LN_v$ pacemaker neurons at ZT23 (FIGS. 10–12). While oscillation of TIM levels in LD does not by itself rule out impairment of the clock (see Price et al. (1998) Cell 94, 83–95), the continued oscillation and nuclear translocation of both TIM and PER suggests that the molecular clock continues to function in at least some respects. Continued molecular oscillation in LD also indicates that electrical silencing does not result in gross non-specific derangement of cellular physiology that prohibits clock function per se. Rather, electrical silencing reveals a specific requirement for electrical activity in the function of the free-running clock, and indicates the existence of a light-dependent drive on the molecular clock that can substitute at least partially for electrical activity in LD.

CRY is a good candidate for a light-dependent drive on the clock that is unimpaired by electrical silencing. CRY has been shown to be involved in cell-autonomously transducing light inputs to the $LN_v$ intracellular clock (Emery et al. (1998) Cell 95, 669–79; Emery et al. (2000) Neuron 26, 493–504; Stanewsky et al. (1998) Cell 95, 681–92). It is also possible that the activation of ligand-gated ion channels or G-protein-coupled metabotropic receptors via light-dependent synaptic inputs to the $LN_v$s might couple directly to the clock without requiring electrical activity.

The present inventors herein demonstrate that electrical activity in the $LN_v$ pacemaker neurons is required for circadian behavioral rhythms. Electrical activity is also required for cycling of the free-running $LN_v$ intracellular clock, but not for cycling of the light-driven clock. These novel features of the interaction between neuronal physiology and the molecular clock pose a number of questions for further inquiry which are addressed below.

What feature of the free-running molecular clock makes it dependent upon electrical activity for continued oscillation? Electrical activity may act as a reinforcing feedback mechanism to keep the clock cycling in the absence of environmental cues. Changes in clock protein levels may be coupled to modulation of membrane electrical activity, which could feed back on clock protein levels. In other words, circadian oscillations in electrical activity could reinforce circadian oscillations in clock protein abundance or function, and vice versa. Light:dark cycles may provide sufficient stimulus to drive the clock such that reinforcing electrical oscillations are not necessary for clock protein oscillations.

How does membrane electrical activity affect cycling of clock proteins? A likely candidate for transducing electrical events at the membrane to intracellular processes central to cycling of the clock is calcium entry through voltage-dependent calcium channels (reviewed by Barish (1998) J Neurobiol 37, 146–57; West et al. (2001) Proc Natl Acad Sci U S A 98, 11024–31). These processes could be mediated by enzymes such as calcium/calmodulin-dependent protein kinases or protein kinase C, or by transcription factors such as CREB, which has already been shown to play a role in *Drosophila* circadian behavior (Barish (1998) supra; Belvin et al. (1999) Neuron 22, 777–87; West et al. (2001) supra). Indeed, intracellular calcium levels and membrane conductance in the pacemaker neurons may oscillate with a circadian rhythm. Such a functional interdependence has been observed in mammals and snails (Colwell (2000) Eur J Neurosci 12, 571–6; Colwell (2001) Eur J Neurosci 13, 1420–8; Michel et al. (1993) Science 259, 239–41; Michel et al. (1999) Bulla. J Biol Rhythms 14, 141–50). The impact of such oscillations may provide means for a regulatory feed back loop on clock activity.

How might clock protein oscillation affect neuronal membrane properties? Ion channels have been demonstrated to be subject to modulation by a diverse set of intracellular signaling pathways (reviewed by Levitan (1999) Neuron 22, 645–8; Ruppersberg (2000) Pflugers Arch 441, 1–11). For example, voltage-gated potassium channels are regulated through protein-protein interactions and covalent modification by stably-associated protein tyrosine kinases (Holmes et al. (1996) Science 274, 2089–91; Nitabach et al. (2001) Proc Natl Acad Sci USA 98, 705–10). Certain inward rectifier potassium channels and voltage-gated calcium channels are modulated by G proteins (Catterall (2000) Annu Rev Cell Dev Biol 16, 521–55; Ruppersberg (2000) supra). It is also likely that clock protein oscillations affect membrane properties by regulating the transcription of ion channel genes or modulatory proteins. Indeed, several *Drosophila* ion channels, including the *Shaker* Kv channel, exhibit clock-dependent circadian oscillations (Claridge-Chang et al. (2001) Neuron 32, 657–71; McDonald and Rosbash (2001) Cell 107, 567–78). The present study demonstrates a previously unappreciated functional connection between oscillation of *Drosophila* pacemaker membrane properties and the cycling of the molecular clock and lays the essential groundwork for future studies.

We claim:

1. A method of reducing or silencing electrical activity in an excitable cell in vitro, comprising:
    (a) introducing a nucleic acid construct encoding an open rectifier K+ channel into an excitable cell selected from the group consisting of a neuron, an endocrine secretory cell, a neuroendocrine secretory cell, a cardiac muscle fiber, a smooth muscle fiber, a skeletal muscle fiber, and a mast cell, wherein the nucleic acid construct comprises a nucleic acid encoding a *Drosophila* open rectifier K+ channel (dORK) that is operably linked to a regulatory element that drives expression of the nucleic acid sequence in the excitable cell, and wherein the electrical activity of an excitable cell is reduced or silenced.

2. The method of claim 1, wherein the excitable cell is a *Drosophila* LN$_v$ pacemaker neuron.

3. The method of claim 1, wherein the nucleic acid comprises the nucleotide sequence of SEQ ID NO: 1.

* * * * *

SEQUENCE LISTING

```
<160> NUMBER OF SEQ ID NOS: 5
<210> SEQ ID NO 1
<211> LENGTH: 3006
<212> TYPE: DNA
<213> ORGANISM: Drosophila

<400> SEQUENCE: 1
atgtcgccga atcgatggat cctgctgctc atcttctaca tatcctacct gatgttcggg      60
gcggcaatct attaccatat tgagcacggc gaggagaaga tatcgcgcgc cgaacagcgc     120
aaggcgcaaa ttgcaatcaa cgaatatctg ctggaggagc tgggcgacaa gaatacgacc     180
acacaggatg agattcttca acggatctcg gattactgtg acaaaccggt tacattgccg     240
ccgacatatg atgatacgcc ctacacgtgg accttctacc atgccttctt cttcgccttc     300
accgtttgct ccacggtggg atatggcaat atatcgccaa ccaccttcgc cggacggatg     360
atcatgatcg cgtattcgt gattggcatc cccgtcaatg gtatcctctt tgccggcctc     420
ggcgaatact ttggacgtac gtttgaagcg atctacagac gctacaaaaa gtacaagatg     480
tccacggata tgcactatgt tccgccgcag ctgggattga tcaccacggt ggtgattgcc     540
ctgattccgg gaatagctct cttcctgctg ctgccctcgt gggtgttcac ctacttcgag     600 aactggcccct attccatctc gctgtactac agctatgtga ccaccacaac aattggattc     660
ggtgactatg tgcccacatt tggagccaac cagcccaagg agttcggcgg ctggttcgtg     720
gtctatcaga tcttttgtgat cgtgtggttc atcttctcgc tgggatatct tgtgatgatc     780
atgacattta tcactcgggg cctccagagc aagaagctgg catacctgga gcagcagttg     840
tcctccaacc tgaaggccac acagaatcgc atctggtctg gcgtcaccaa ggatgtgggc     900
tacctccggc gaatgctcaa cgagctgtac atcctcaaag tgaagcctgt gtacaccgat     960
gtagatatcg cctacacact gccacgttcc aattcgtgtc cggatctgag catgtaccgc    1020
gtggagccgg ctcccattcc cagccggaag agggcattct ccgtgtgcgc cgacatggtt    1080
gccgcccaaa gggaggcggg catggtacac gccaattccg atacggagct aagcaaactg    1140
gatcgcgaga agacattcga gacggcggag gcgtaccgcc agaccaccga tttgctggcc    1200
aaggtggtca acgcactggc cacggtgaag ccaccgccgg cggaacagga agatgcggct    1260
ctctatggtg gctatcatgg cttctccgac tcccagatcc tggccagcga atggtcgttc    1320
tcgacggtca acgagttcac atcaccgcga cgtccaagag cacgtgcctg ctccgatttc    1380
aatctggagg cacctcgctg gcagagcgag aggccactgc gttcgagcca caacgaatgg    1440
acatggagcg gcgacaacca gcagatccag gaggcattca accagcgcta caagggacag    1500
cagcgtgcca acggagcagc caactcgacc atggtccatc tggagccgga tgctttggag    1560
gagcagctga agaaacaatc accggtgcc ggtcgcgtca agaagttctc catgccggat    1620
ggtctgcgac gtcgtttcc cttccagaag aagcgcccct cgcaggatct ggagcgcaag    1680
ttgtccgtgg tctcggtacc cgagggtgtc atctcgcagc aagccagatc cccgctggac    1740
```

```
tactacagca acacggtcac ggcggcctcc agtcaatcct atttgcgcaa cggacgcggt    1800
ccgccaccgc ccttcgaatc gaatggcagc ttggccagcg gcggcggcgg gctaacgaac    1860
atgggcttcc agatggagga tggagcaacc ccgccatcgg cattgggcgg tggagcctat    1920
caacgcaagg cggctgctgg caagcgccga cgcgagagca tctacaccca gaatcaagcc    1980
ccatccgctc gccggggcag catgtatccg ccgaccgcgc acgccttggc ccagatgcag    2040
atgcgacgcg gcagcttggc aaccagtggc tctggatcgg cggccatggc ggcagtggcc    2100
gcgcgtcgtg gcagcctctt cccagctaca gcatcggcat catcgctgac ctctgctccg    2160
cgccgtagca gcatattctc ggttacctcc gaaaaggata tgaatgtgct ggagcagacg    2220
accattgcgg atctgattcg tgcgctcgag gtagtgcaca cccatgccgt gcttgatgaa    2280
cagcaacagg cggcagcggc tggaggagct gccggtggag gcggaatatc gaggggtagc    2340
cgcaaacagc gcaagatggg caatgctgga ctggagccac cgcagctgcc gccgatcctg    2400
tcgctctttg ctggcgatca acgaggaca ctgcaggcgg cggctgccaa tcggctgtac    2460
```

(Note: line at 2460 reads "ctggcgatca acgaggaca ctgcaggcgg" — preserving as shown)

```
gcgcgtcgct ccactattgt tggcatatcg cccactggtg gagcagccac cgcaccggca    2520
gccagatccc tgctggaacc gccacccagt tacactgaga gagccgcaaa tcaaagccaa    2580
ataacagccg gtccatcgaa tgcgccaact gttcagagca aattccgtcg tcgctttagc    2640
gtgcgaccga ctgctctgca aattccaccg ggacaggcgc cgccaccagg tgccagtttg    2700
atggagcagt cctcacagac ggcgctccag cgacgcctct cgctgcgacc ctcgccactg    2760
gcccgcgaac tgtcgcccac gtcgccgccc ggaggaagtg gaagcgcctt gccagcgggg    2820
gccatcgacg agtctggcgg aacgtccgct caacggctgc tgcccttgcc cgccggaacg    2880
agacccagca ccagcagcac ccactcgccg ctctcgagga tcgtgcagat ctcgcaagca    2940
cagcgcaaga gcagcatgcc cagtgcagcg gccacgggat cgagtggtgc ccccgccgag    3000
aagtag                                                             3006
```

<210> SEQ ID NO 2
<211> LENGTH: 1001
<212> TYPE: PRT
<213> ORGANISM: Drosophila

<400> SEQUENCE: 2

```
Met Ser Pro Asn Arg Trp Ile Leu Leu Ile Phe Tyr Ile Ser Tyr
  1               5                  10                  15

Leu Met Phe Gly Ala Ala Ile Tyr Tyr His Ile Glu His Gly Glu Glu
             20                  25                  30

Lys Ile Ser Arg Ala Glu Gln Arg Lys Ala Gln Ile Ala Ile Asn Glu
         35                  40                  45

Tyr Leu Leu Glu Glu Leu Gly Asp Lys Asn Thr Thr Thr Gln Asp Glu
     50                  55                  60

Ile Leu Gln Arg Ile Ser Asp Tyr Cys Asp Lys Pro Val Thr Leu Pro
 65                  70                  75                  80

Pro Thr Tyr Asp Asp Thr Pro Tyr Thr Trp Thr Phe Tyr His Ala Phe
                 85                  90                  95

Phe Phe Ala Phe Thr Val Cys Ser Thr Val Ala Ala Asn Ile Ser
            100                 105                 110

Pro Thr Thr Phe Ala Gly Arg Met Ile Met Ile Ala Tyr Ser Val Ile
        115                 120                 125

Gly Ile Pro Val Asn Gly Ile Leu Phe Ala Gly Leu Gly Glu Tyr Phe
    130                 135                 140
```

```
Gly Arg Thr Phe Glu Ala Ile Tyr Arg Arg Tyr Lys Lys Tyr Lys Met
145                 150                 155                 160

Ser Thr Asp Met His Tyr Val Pro Pro Gln Leu Gly Leu Ile Thr Thr
                165                 170                 175

Val Val Ile Ala Leu Ile Pro Gly Ile Ala Leu Phe Leu Leu Leu Pro
            180                 185                 190

Ser Trp Val Phe Thr Tyr Phe Glu Asn Trp Pro Tyr Ser Ile Ser Leu
        195                 200                 205

Tyr Tyr Ser Tyr Val Thr Thr Thr Ile Gly Phe Gly Asp Tyr Val
210                 215                 220

Pro Thr Phe Gly Ala Asn Gln Pro Lys Glu Phe Gly Gly Trp Phe Val
225                 230                 235                 240

Val Tyr Gln Ile Phe Val Ile Val Trp Phe Ile Phe Ser Leu Gly Tyr
                245                 250                 255

Leu Val Met Ile Met Thr Phe Ile Thr Arg Gly Leu Gln Ser Lys Lys
            260                 265                 270

Leu Ala Tyr Leu Glu Gln Gln Leu Ser Ser Asn Leu Lys Ala Thr Gln
        275                 280                 285

Asn Arg Ile Trp Ser Gly Val Thr Lys Asp Val Gly Tyr Leu Arg Arg
290                 295                 300

Met Leu Asn Glu Leu Tyr Ile Leu Lys Val Lys Pro Val Tyr Thr Asp
305                 310                 315                 320

Val Asp Ile Ala Tyr Thr Leu Pro Arg Ser Asn Ser Cys Pro Asp Leu
                325                 330                 335

Ser Met Tyr Arg Val Glu Pro Ala Pro Ile Pro Ser Arg Lys Arg Ala
            340                 345                 350

Phe Ser Val Cys Ala Asp Met Val Ala Ala Gln Arg Glu Ala Gly Met
        355                 360                 365

Val His Ala Asn Ser Asp Thr Glu Leu Ser Lys Leu Asp Arg Glu Lys
370                 375                 380

Thr Phe Glu Thr Ala Glu Ala Tyr Arg Gln Thr Thr Asp Leu Leu Ala
385                 390                 395                 400

Lys Val Val Asn Ala Leu Ala Thr Val Lys Pro Pro Ala Glu Gln
                405                 410                 415

Glu Asp Ala Ala Leu Tyr Gly Gly Tyr His Gly Phe Ser Asp Ser Gln
            420                 425                 430

Ile Leu Ala Ser Glu Trp Ser Phe Ser Thr Val Asn Glu Phe Thr Ser
        435                 440                 445

Pro Arg Arg Pro Arg Ala Arg Ala Cys Ser Asp Phe Asn Leu Glu Ala
450                 455                 460

Pro Arg Trp Gln Ser Glu Arg Pro Leu Arg Ser Ser His Asn Glu Trp
465                 470                 475                 480

Thr Trp Ser Gly Asp Asn Gln Gln Ile Gln Glu Ala Phe Asn Gln Arg
                485                 490                 495

Tyr Lys Gly Gln Gln Arg Ala Asn Gly Ala Ala Asn Ser Thr Met Val
            500                 505                 510

His Leu Glu Pro Asp Ala Leu Glu Glu Gln Leu Lys Lys Gln Ser Pro
        515                 520                 525

Gly Ala Gly Arg Val Lys Lys Phe Ser Met Pro Asp Gly Leu Arg Arg
530                 535                 540

Leu Phe Pro Phe Gln Lys Lys Arg Pro Ser Gln Asp Leu Glu Arg Lys
545                 550                 555                 560
```

-continued

```
Leu Ser Val Val Ser Val Pro Glu Gly Val Ile Ser Gln Gln Ala Arg
                565                 570                 575
Ser Pro Leu Asp Tyr Tyr Ser Asn Thr Val Thr Ala Ala Ser Ser Gln
            580                 585                 590
Ser Tyr Leu Arg Asn Gly Arg Gly Pro Pro Pro Phe Glu Ser Asn
        595                 600                 605
Gly Ser Leu Ala Ser Gly Gly Gly Leu Thr Asn Met Gly Phe Gln
    610                 615                 620
Met Glu Asp Gly Ala Thr Pro Pro Ser Ala Leu Gly Gly Gly Ala Tyr
625                 630                 635                 640
Gln Arg Lys Ala Ala Gly Lys Arg Arg Glu Ser Ile Tyr Thr
                645                 650                 655
Gln Asn Gln Ala Pro Ser Ala Arg Arg Gly Ser Met Tyr Pro Pro Thr
            660                 665                 670
Ala His Ala Leu Ala Gln Met Gln Met Arg Arg Gly Ser Leu Ala Thr
        675                 680                 685
Ser Gly Ser Gly Ser Ala Ala Met Ala Ala Val Ala Ala Arg Arg Gly
    690                 695                 700
Ser Leu Phe Pro Ala Thr Ala Ser Ala Ser Leu Thr Ser Ala Pro
705                 710                 715                 720
Arg Arg Ser Ser Ile Phe Ser Val Thr Ser Glu Lys Asp Met Asn Val
                725                 730                 735
Leu Glu Gln Thr Thr Ile Ala Asp Leu Ile Arg Ala Leu Glu Val Val
            740                 745                 750
His Thr His Ala Val Leu Asp Glu Gln Gln Gln Ala Ala Ala Ala Gly
        755                 760                 765
Gly Ala Ala Gly Gly Gly Ile Ser Arg Gly Ser Arg Lys Gln Arg
    770                 775                 780
Lys Met Gly Asn Ala Gly Leu Glu Pro Pro Gln Leu Pro Pro Ile Leu
785                 790                 795                 800
Ser Leu Phe Ala Gly Asp Gln Thr Arg Thr Leu Gln Ala Ala Ala Ala
                805                 810                 815
Asn Arg Leu Tyr Ala Arg Arg Ser Thr Ile Val Gly Ile Ser Pro Thr
            820                 825                 830
Gly Gly Ala Ala Thr Ala Pro Ala Ala Arg Ser Leu Leu Glu Pro Pro
        835                 840                 845
Pro Ser Tyr Thr Glu Arg Ala Ala Asn Gln Ser Gln Ile Thr Ala Gly
    850                 855                 860
Pro Ser Asn Ala Pro Thr Val Gln Ser Lys Phe Arg Arg Phe Ser
865                 870                 875                 880
Val Arg Pro Thr Ala Leu Gln Ile Pro Pro Gly Gln Ala Pro Pro Pro
                885                 890                 895
Gly Ala Ser Leu Met Glu Gln Ser Ser Gln Thr Ala Leu Gln Arg Arg
            900                 905                 910
Leu Ser Leu Arg Pro Ser Pro Leu Ala Arg Glu Leu Ser Pro Thr Ser
        915                 920                 925
Pro Pro Gly Gly Ser Gly Ser Ala Leu Pro Ala Gly Ala Ile Asp Glu
    930                 935                 940
Ser Gly Gly Thr Ser Ala Gln Arg Leu Leu Pro Leu Pro Ala Gly Thr
945                 950                 955                 960
Arg Pro Ser Thr Ser Ser Thr His Ser Pro Leu Ser Arg Ile Val Gln
                965                 970                 975
```

-continued

```
Ile Ser Gln Ala Gln Arg Lys Ser Ser Met Pro Ser Ala Ala Ala Thr
            980                 985                 990
Gly Ser Ser Gly Ala Pro Ala Glu Lys
            995                 1000
```

<210> SEQ ID NO 3
<211> LENGTH: 897
<212> TYPE: DNA
<213> ORGANISM: Drosophila

<400> SEQUENCE: 3

```
atgtcgccga atcgatggat cctgctgctc atcttctaca tatcctacct gatgttcggg      60
gcggcaatct attaccatat tgagcacggc gaggagaaga tatcgcgcgc cgaacagcgc     120
aaggcgcaaa ttgcaatcaa cgaatatctg ctggaggagc tgggcgacaa gaatacgacc     180
acacaggatg agattcttca acggatctcg gattactgtg acaaaccggt tacattgccg     240
ccgacatatg atgatacgcc ctacacgtgg accttctacc atgccttctt cttcgccttc     300
accgtttgct ccacggtggg atatggcaat atatcgccaa ccaccttcgc cggacggatg     360
atcatgatcg cgtattcggt gattggcatc cccgtcaatg gtatcctctt tgccggcctc     420
ggcgaatact ttggacgtac gtttgaagcg atctacagac gctacaaaaa gtacaagatg     480
tccacggata tgcactatgt tccgccgcag ctgggattga tcaccacggt ggtgattgcc     540
ctgattccgg aatagctct cttcctgctg ctgccctcgt gggtgttcac ctacttcgag     600
aactggccct attccatctc gctgtactac agctatgtga ccaccacaac aattggattc     660
ggtgactatg tgcccacatt tggagccaac cagcccaagg agttcggcgg ctggttcgtg     720
gtctatcaga tctttgtgat cgtgtggttc atcttctcgc tgggatatct tgtgatgatc     780
atgacattta tcactcgggg cctccagagc aagaagctgg cataacctgga gcagcagttg     840
tcctccaacc tgaaggccac acagaatcgc atctggtctg gcgtcaccaa ggattaa        897
```

<210> SEQ ID NO 4
<211> LENGTH: 1001
<212> TYPE: PRT
<213> ORGANISM: Drosophila

<400> SEQUENCE: 4

```
Met Ser Pro Asn Arg Trp Ile Leu Leu Ile Phe Tyr Ile Ser Tyr
  1               5                  10                  15
Leu Met Phe Gly Ala Ala Ile Tyr Tyr His Ile Glu His Gly Glu Glu
             20                  25                  30
Lys Ile Ser Arg Ala Glu Gln Arg Lys Ala Gln Ile Ala Ile Asn Glu
         35                  40                  45
Tyr Leu Leu Glu Glu Leu Gly Asp Lys Asn Thr Thr Thr Gln Asp Glu
     50                  55                  60
Ile Leu Gln Arg Ile Ser Asp Tyr Cys Asp Lys Pro Val Thr Leu Pro
 65                  70                  75                  80
Pro Thr Tyr Asp Asp Thr Pro Tyr Thr Trp Thr Phe Tyr His Ala Phe
                 85                  90                  95
Phe Phe Ala Phe Thr Val Cys Ser Thr Val Gly Tyr Gly Asn Ile Ser
            100                 105                 110
Pro Thr Thr Phe Ala Gly Arg Met Ile Met Ile Ala Tyr Ser Val Ile
        115                 120                 125
Gly Ile Pro Val Asn Gly Ile Leu Phe Ala Gly Leu Gly Glu Tyr Phe
    130                 135                 140
```

-continued

```
Gly Arg Thr Phe Glu Ala Ile Tyr Arg Arg Tyr Lys Lys Tyr Lys Met
145                 150                 155                 160

Ser Thr Asp Met His Tyr Val Pro Pro Gln Leu Gly Leu Ile Thr Thr
                165                 170                 175

Val Val Ile Ala Leu Ile Pro Gly Ile Ala Leu Phe Leu Leu Leu Pro
            180                 185                 190

Ser Trp Val Phe Thr Tyr Phe Glu Asn Trp Pro Tyr Ser Ile Ser Leu
        195                 200                 205

Tyr Tyr Ser Tyr Val Thr Thr Thr Ile Gly Phe Gly Asp Tyr Val
    210                 215                 220

Pro Thr Phe Gly Ala Asn Gln Pro Lys Glu Phe Gly Gly Trp Phe Val
225                 230                 235                 240

Val Tyr Gln Ile Phe Val Ile Val Trp Phe Ile Phe Ser Leu Gly Tyr
                245                 250                 255

Leu Val Met Ile Met Thr Phe Ile Thr Arg Gly Leu Gln Ser Lys Lys
                260                 265                 270

Leu Ala Tyr Leu Glu Gln Gln Leu Ser Ser Asn Leu Lys Ala Thr Gln
            275                 280                 285

Asn Arg Ile Trp Ser Gly Val Thr Lys Asp Val Gly Tyr Leu Arg Arg
290                 295                 300

Met Leu Asn Glu Leu Tyr Ile Leu Lys Val Lys Pro Val Tyr Thr Asp
305                 310                 315                 320

Val Asp Ile Ala Tyr Thr Leu Pro Arg Ser Asn Ser Cys Pro Asp Leu
                325                 330                 335

Ser Met Tyr Arg Val Glu Pro Ala Pro Ile Pro Ser Arg Lys Arg Ala
                340                 345                 350

Phe Ser Val Cys Ala Asp Met Val Ala Ala Gln Arg Glu Ala Gly Met
                355                 360                 365

Val His Ala Asn Ser Asp Thr Glu Leu Ser Lys Leu Asp Arg Glu Lys
    370                 375                 380

Thr Phe Glu Thr Ala Glu Ala Tyr Arg Gln Thr Thr Asp Leu Leu Ala
385                 390                 395                 400

Lys Val Val Asn Ala Leu Ala Thr Val Lys Pro Pro Ala Glu Gln
                405                 410                 415

Glu Asp Ala Ala Leu Tyr Gly Gly Tyr His Gly Phe Ser Asp Ser Gln
            420                 425                 430

Ile Leu Ala Ser Glu Trp Ser Phe Ser Thr Val Asn Glu Phe Thr Ser
                435                 440                 445

Pro Arg Arg Pro Arg Ala Arg Ala Cys Ser Asp Phe Asn Leu Glu Ala
450                 455                 460

Pro Arg Trp Gln Ser Glu Arg Pro Leu Arg Ser Ser His Asn Glu Trp
465                 470                 475                 480

Thr Trp Ser Gly Asp Asn Gln Gln Ile Gln Glu Ala Phe Asn Gln Arg
                485                 490                 495

Tyr Lys Gly Gln Gln Arg Ala Asn Gly Ala Ala Asn Ser Thr Met Val
            500                 505                 510

His Leu Glu Pro Asp Ala Leu Glu Glu Gln Leu Lys Lys Gln Ser Pro
            515                 520                 525

Gly Ala Gly Arg Val Lys Lys Phe Ser Met Pro Asp Gly Leu Arg Arg
530                 535                 540

Leu Phe Pro Phe Gln Lys Lys Arg Pro Ser Gln Asp Leu Glu Arg Lys
545                 550                 555                 560
```

-continued

```
Leu Ser Val Val Ser Val Pro Glu Gly Val Ile Ser Gln Gln Ala Arg
                565                 570                 575
Ser Pro Leu Asp Tyr Tyr Ser Asn Thr Val Thr Ala Ala Ser Ser Gln
            580                 585                 590
Ser Tyr Leu Arg Asn Gly Arg Gly Pro Pro Pro Phe Glu Ser Asn
        595                 600                 605
Gly Ser Leu Ala Ser Gly Gly Gly Leu Thr Asn Met Gly Phe Gln
    610                 615                 620
Met Glu Asp Gly Ala Thr Pro Pro Ser Ala Leu Gly Gly Ala Tyr
625                 630                 635                 640
Gln Arg Lys Ala Ala Gly Lys Arg Arg Glu Ser Ile Tyr Thr
                645                 650                 655
Gln Asn Gln Ala Pro Ser Ala Arg Arg Gly Ser Met Tyr Pro Pro Thr
            660                 665                 670
Ala His Ala Leu Ala Gln Met Gln Met Arg Arg Gly Ser Leu Ala Thr
        675                 680                 685
Ser Gly Ser Gly Ser Ala Ala Met Ala Ala Val Ala Ala Arg Arg Gly
    690                 695                 700
Ser Leu Phe Pro Ala Thr Ala Ser Ala Ser Leu Thr Ser Ala Pro
705                 710                 715                 720
Arg Arg Ser Ser Ile Phe Ser Val Thr Ser Glu Lys Asp Met Asn Val
                725                 730                 735
Leu Glu Gln Thr Thr Ile Ala Asp Leu Ile Arg Ala Leu Glu Val Val
            740                 745                 750
His Thr His Ala Val Leu Asp Glu Gln Gln Gln Ala Ala Ala Ala Gly
        755                 760                 765
Gly Ala Ala Gly Gly Gly Ile Ser Arg Gly Ser Arg Lys Gln Arg
    770                 775                 780
Lys Met Gly Asn Ala Gly Leu Glu Pro Pro Gln Leu Pro Pro Ile Leu
785                 790                 795                 800
Ser Leu Phe Ala Gly Asp Gln Thr Arg Thr Leu Gln Ala Ala Ala Ala
                805                 810                 815
Asn Arg Leu Tyr Ala Arg Arg Ser Thr Ile Val Gly Ile Ser Pro Thr
            820                 825                 830
Gly Gly Ala Ala Thr Ala Pro Ala Ala Arg Ser Leu Leu Glu Pro Pro
        835                 840                 845
Pro Ser Tyr Thr Glu Arg Ala Ala Asn Gln Ser Gln Ile Thr Ala Gly
    850                 855                 860
Pro Ser Asn Ala Pro Thr Val Gln Ser Lys Phe Arg Arg Phe Ser
865                 870                 875                 880
Val Arg Pro Thr Ala Leu Gln Ile Pro Pro Gly Gln Ala Pro Pro
                885                 890                 895
Gly Ala Ser Leu Met Glu Gln Ser Ser Gln Thr Ala Leu Gln Arg Arg
            900                 905                 910
Leu Ser Leu Arg Pro Ser Pro Leu Ala Arg Glu Leu Ser Pro Thr Ser
        915                 920                 925
Pro Pro Gly Gly Ser Gly Ser Ala Leu Pro Ala Gly Ala Ile Asp Glu
    930                 935                 940
Ser Gly Gly Thr Ser Ala Gln Arg Leu Leu Pro Leu Pro Ala Gly Thr
945                 950                 955                 960
Arg Pro Ser Thr Ser Ser Thr His Ser Pro Leu Ser Arg Ile Val Gln
                965                 970                 975
```

```
Ile Ser Gln Ala Gln Arg Lys Ser Ser Met Pro Ser Ala Ala Ala Thr
            980                 985                 990

Gly Ser Ser Gly Ala Pro Ala Glu Lys
            995                 1000

<210> SEQ ID NO 5
<211> LENGTH: 1001
<212> TYPE: PRT
<213> ORGANISM: Drosophila

<400> SEQUENCE: 5

Met Ser Pro Asn Arg Trp Ile Leu Leu Ile Phe Tyr Ile Ser Tyr
 1               5                  10                  15

Leu Met Phe Gly Ala Ala Ile Tyr Tyr His Ile Glu His Gly Glu Glu
                20                  25                  30

Lys Ile Ser Arg Ala Glu Gln Arg Lys Ala Gln Ile Ala Ile Asn Glu
                35                  40                  45

Tyr Leu Leu Glu Glu Leu Gly Asp Lys Asn Thr Thr Thr Gln Asp Glu
 50                  55                  60

Ile Leu Gln Arg Ile Ser Asp Tyr Cys Asp Lys Pro Val Thr Leu Pro
65                   70                  75                  80

Pro Thr Tyr Asp Asp Thr Pro Tyr Thr Trp Thr Phe Tyr His Ala Phe
                85                  90                  95

Phe Phe Ala Phe Thr Val Cys Ser Thr Val Gly Tyr Gly Asn Ile Ser
                100                 105                 110

Pro Thr Thr Phe Ala Gly Arg Met Ile Met Ile Ala Tyr Ser Val Ile
                115                 120                 125

Gly Ile Pro Val Asn Gly Ile Leu Phe Ala Gly Leu Gly Glu Tyr Phe
                130                 135                 140

Gly Arg Thr Phe Glu Ala Ile Tyr Arg Arg Tyr Lys Lys Tyr Lys Met
145                 150                 155                 160

Ser Thr Asp Met His Tyr Val Pro Pro Gln Leu Gly Leu Ile Thr Thr
                165                 170                 175

Val Val Ile Ala Leu Ile Pro Gly Ile Ala Leu Phe Leu Leu Leu Pro
                180                 185                 190

Ser Trp Val Phe Thr Tyr Phe Glu Asn Trp Pro Tyr Ser Ile Ser Leu
                195                 200                 205

Tyr Tyr Ser Tyr Val Thr Thr Thr Thr Ile Ala Ala Ala Asp Tyr Val
                210                 215                 220

Pro Thr Phe Gly Ala Asn Gln Pro Lys Glu Phe Gly Gly Trp Phe Val
225                 230                 235                 240

Val Tyr Gln Ile Phe Val Ile Val Trp Phe Ile Phe Ser Leu Gly Tyr
                245                 250                 255

Leu Val Met Ile Met Thr Phe Ile Thr Arg Gly Leu Gln Ser Lys Lys
                260                 265                 270

Leu Ala Tyr Leu Glu Gln Gln Leu Ser Ser Asn Leu Lys Ala Thr Gln
                275                 280                 285

Asn Arg Ile Trp Ser Gly Val Thr Lys Asp Val Gly Tyr Leu Arg Arg
                290                 295                 300

Met Leu Asn Glu Leu Tyr Ile Leu Lys Val Lys Pro Val Tyr Thr Asp
305                 310                 315                 320

Val Asp Ile Ala Tyr Thr Leu Pro Arg Ser Asn Ser Cys Pro Asp Leu
                325                 330                 335

Ser Met Tyr Arg Val Glu Pro Ala Pro Ile Pro Ser Arg Lys Arg Ala
                340                 345                 350
```

```
Phe Ser Val Cys Ala Asp Met Val Ala Gln Arg Glu Ala Gly Met
        355                 360                 365

Val His Ala Asn Ser Asp Thr Glu Leu Ser Lys Leu Asp Arg Glu Lys
    370                 375                 380

Thr Phe Glu Thr Ala Glu Ala Tyr Arg Gln Thr Thr Asp Leu Leu Ala
385                 390                 395                 400

Lys Val Val Asn Ala Leu Ala Thr Val Lys Pro Pro Ala Glu Gln
                405                 410                 415

Glu Asp Ala Ala Leu Tyr Gly Tyr His Gly Phe Ser Asp Ser Gln
                420                 425                 430

Ile Leu Ala Ser Glu Trp Ser Phe Ser Thr Val Asn Glu Phe Thr Ser
        435                 440                 445

Pro Arg Arg Pro Arg Ala Arg Ala Cys Ser Asp Phe Asn Leu Glu Ala
    450                 455                 460

Pro Arg Trp Gln Ser Glu Arg Pro Leu Arg Ser Ser His Asn Glu Trp
465                 470                 475                 480

Thr Trp Ser Gly Asp Asn Gln Gln Ile Gln Glu Ala Phe Asn Gln Arg
                485                 490                 495

Tyr Lys Gly Gln Gln Arg Ala Asn Gly Ala Ala Asn Ser Thr Met Val
                500                 505                 510

His Leu Glu Pro Asp Ala Leu Glu Glu Gln Leu Lys Lys Gln Ser Pro
    515                 520                 525

Gly Ala Gly Arg Val Lys Lys Phe Ser Met Pro Asp Gly Leu Arg Arg
    530                 535                 540

Leu Phe Pro Phe Gln Lys Lys Arg Pro Ser Gln Asp Leu Glu Arg Lys
545                 550                 555                 560

Leu Ser Val Val Ser Val Pro Glu Gly Val Ile Ser Gln Gln Ala Arg
                565                 570                 575

Ser Pro Leu Asp Tyr Tyr Ser Asn Thr Val Thr Ala Ala Ser Ser Gln
                580                 585                 590

Ser Tyr Leu Arg Asn Gly Arg Gly Pro Pro Pro Phe Glu Ser Asn
    595                 600                 605

Gly Ser Leu Ala Ser Gly Gly Gly Leu Thr Asn Met Gly Phe Gln
    610                 615                 620

Met Glu Asp Gly Ala Thr Pro Pro Ser Ala Leu Gly Gly Gly Ala Tyr
625                 630                 635                 640

Gln Arg Lys Ala Ala Ala Gly Lys Arg Arg Glu Ser Ile Tyr Thr
                645                 650                 655

Gln Asn Gln Ala Pro Ser Ala Arg Arg Gly Ser Met Tyr Pro Pro Thr
    660                 665                 670

Ala His Ala Leu Ala Gln Met Gln Met Arg Arg Gly Ser Leu Ala Thr
    675                 680                 685

Ser Gly Ser Gly Ser Ala Ala Met Ala Ala Val Ala Ala Arg Arg Gly
    690                 695                 700

Ser Leu Phe Pro Ala Thr Ala Ser Ala Ser Ser Leu Thr Ser Ala Pro
705                 710                 715                 720

Arg Arg Ser Ser Ile Phe Ser Val Thr Ser Glu Lys Asp Met Asn Val
                725                 730                 735

Leu Glu Gln Thr Thr Ile Ala Asp Leu Ile Arg Ala Leu Glu Val Val
                740                 745                 750

His Thr His Ala Val Leu Asp Glu Gln Gln Gln Ala Ala Ala Ala Gly
        755                 760                 765
```

-continued

```
Gly Ala Ala Gly Gly Gly Ile Ser Arg Gly Ser Arg Lys Gln Arg
        770             775             780

Lys Met Gly Asn Ala Gly Leu Glu Pro Pro Gln Leu Pro Pro Ile Leu
785             790             795                     800

Ser Leu Phe Ala Gly Asp Gln Thr Arg Thr Leu Gln Ala Ala Ala Ala
            805             810                 815

Asn Arg Leu Tyr Ala Arg Arg Ser Thr Ile Val Gly Ile Ser Pro Thr
            820             825                 830

Gly Gly Ala Ala Thr Ala Pro Ala Ala Arg Ser Leu Leu Glu Pro Pro
            835             840             845

Pro Ser Tyr Thr Glu Arg Ala Ala Asn Gln Ser Gln Ile Thr Ala Gly
        850             855             860

Pro Ser Asn Ala Pro Thr Val Gln Ser Lys Phe Arg Arg Arg Phe Ser
865             870             875                     880

Val Arg Pro Thr Ala Leu Gln Ile Pro Pro Gly Gln Ala Pro Pro Pro
            885             890                 895

Gly Ala Ser Leu Met Glu Gln Ser Ser Gln Thr Ala Leu Gln Arg Arg
            900             905             910

Leu Ser Leu Arg Pro Ser Pro Leu Ala Arg Glu Leu Ser Pro Thr Ser
            915             920             925

Pro Pro Gly Gly Ser Gly Ser Ala Leu Pro Ala Gly Ala Ile Asp Glu
        930             935             940

Ser Gly Gly Thr Ser Ala Gln Arg Leu Leu Pro Leu Pro Ala Gly Thr
945             950             955                     960

Arg Pro Ser Thr Ser Ser Thr His Ser Pro Leu Ser Arg Ile Val Gln
            965             970             975

Ile Ser Gln Ala Gln Arg Lys Ser Ser Met Pro Ser Ala Ala Ala Thr
            980             985             990

Gly Ser Ser Gly Ala Pro Ala Glu Lys
        995             1000
```